United States Patent [19]
Girone et al.

[11] Patent Number: 6,162,189
[45] Date of Patent: Dec. 19, 2000

[54] ANKLE REHABILITATION SYSTEM

[75] Inventors: Michael John Girone, Edison; Grigore Burdea, Highland Park; Mourad Bouzit, Somerset, all of N.J.

[73] Assignee: Rutgers, The State University of New Jersey, Piscataway, N.J.

[21] Appl. No.: 09/320,639

[22] Filed: May 26, 1999

[51] Int. Cl.[7] .................................................. A61B 5/103
[52] U.S. Cl. .......................... 600/592; 600/587; 600/595; 482/79
[58] Field of Search .................................... 600/587, 592, 600/595; 33/515; 482/34, 79, 80

[56] References Cited

U.S. PATENT DOCUMENTS

| | | | |
|---|---|---|---|
| 4,605,220 | 8/1986 | Troxel | 272/96 |
| 4,802,494 | 2/1989 | Gardiner | 600/592 |
| 5,168,634 | 12/1992 | Misevich | 33/515 |
| 5,271,876 | 12/1993 | Ibar | 264/22 |
| 5,312,315 | 5/1994 | Mortensen et al. | 482/113 |
| 5,335,674 | 8/1994 | Siegler | 600/595 |
| 5,354,162 | 10/1994 | Burdea et al. | 414/5 |
| 5,360,015 | 11/1994 | Heurte | 600/595 |
| 5,402,800 | 4/1995 | Hollis | 128/779 |
| 5,429,140 | 7/1995 | Burdea et al. | 128/774 |
| 5,441,047 | 8/1995 | David et al. | 128/670 |
| 5,474,090 | 12/1995 | Begun et al. | 128/707 |
| 5,482,051 | 1/1996 | Reddy et al. | 128/733 |
| 5,518,476 | 5/1996 | McLeon | 382/79 |
| 5,577,981 | 11/1996 | Jarvik | 482/4 |
| 5,598,849 | 2/1997 | Browne | 128/707 |
| 5,619,991 | 4/1997 | Sloane | 128/630 |
| 5,629,594 | 5/1997 | Jacobus et al. | 318/568.11 |
| 5,711,671 | 1/1998 | Geeslin et al. | 434/236 |
| 5,737,505 | 4/1998 | Shaw et al. | 395/119 |
| 5,754,121 | 5/1998 | Ward et al. | 340/870.09 |
| 5,785,650 | 7/1998 | Akasaka et al. | 600/300 |
| 5,805,137 | 9/1998 | Yasutake | 345/156 |
| 5,810,747 | 9/1998 | Brudny et al. | 600/595 |
| 5,902,214 | 5/1999 | Makikawa et al. | 482/4 |
| 5,987,726 | 11/1999 | Akeel | 29/407.08 |
| 6,063,046 | 5/2000 | Allum | 600/595 |

OTHER PUBLICATIONS

Stewart, D. "A platform with six degrees of freedom." The Institution of Mechanical Engineers Proceedings, vol. 180, Part 1, No. 15, 1965–66.

*Primary Examiner*—Cary O'Connor
*Assistant Examiner*—Charles Marmor, II
*Attorney, Agent, or Firm*—Mathews, Collins, Shepherd & Gould P.A.

[57] ABSTRACT

The present invention relates to a system for rehabilitating an ankle in which a mobile platform receives a patient's foot. The mobile platform can be moved in six degrees of freedom. The position and orientation of the mobile platform is measured in relation to the fixed platform in six degrees of freedom. The force exerted by the foot against the mobile platform is measured in six degrees of freedom. The measured position and measured force are forwarded to an electronic interface and fed to a programmable computer. The programmable computer determines desired force feedback to be applied by the controller interface to the mobile platform. The desired feedback signal moves the mobile platform to a desired position or applies a desired force or torque to the mobile platform. The rehabilitation system can include simulation of virtual objects which can be moved by the user to simulate an exercise. For example, the virtual reality simulation can include exercises for balance, flexibility and strength. The system can be remotely controlled in a telerehabilitation environment.

31 Claims, 24 Drawing Sheets

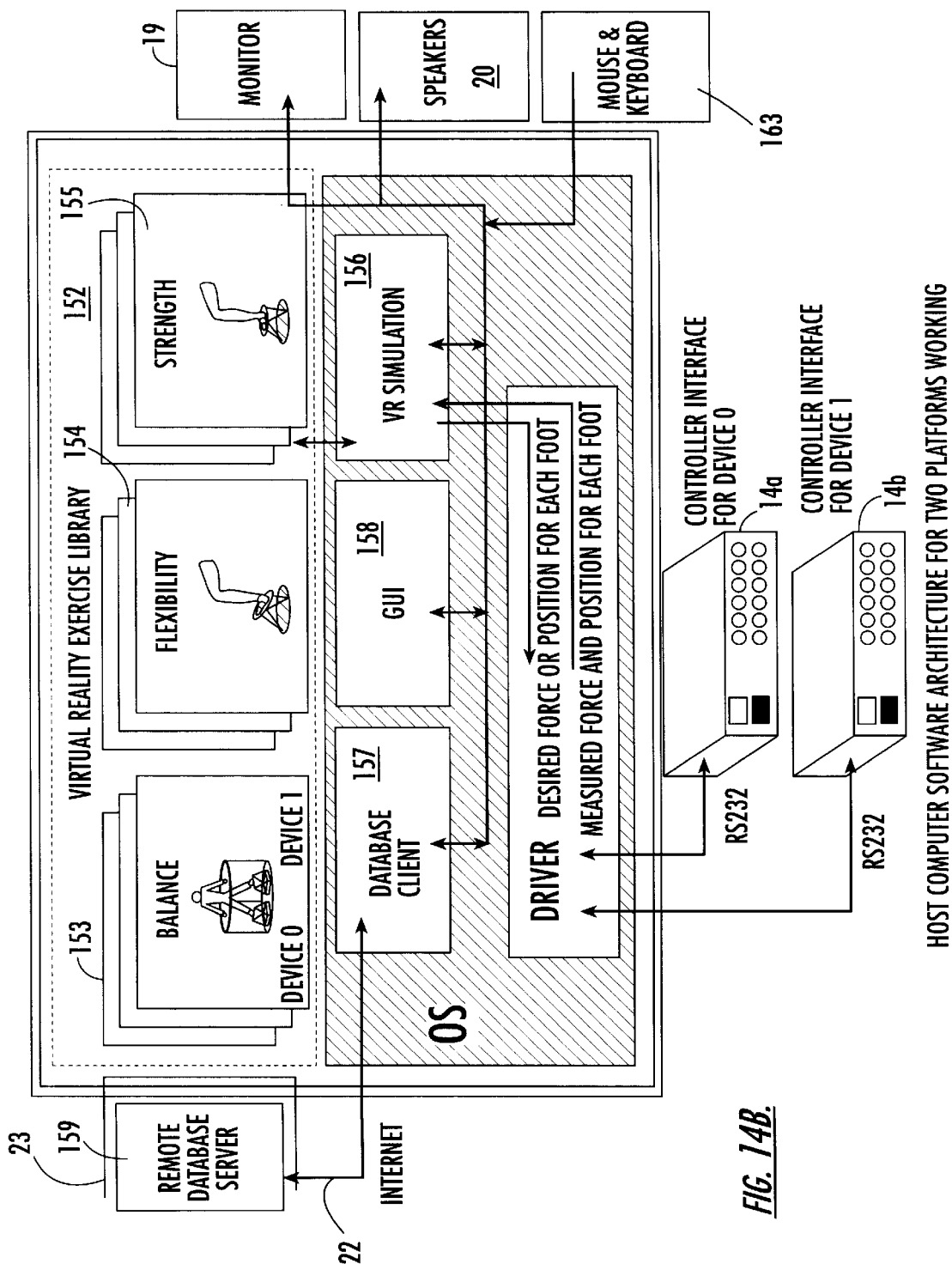

ANKLE REHABILITATION SYSTEM

BACKGROUND OF THE INVENTION

1. Field of the Invention

The present invention relates to a rehabilitation system and method in which the position of the ankle is determined and force feedback is applied for the six-degrees of freedom of the ankle.

2. Related Art

Injuries to the lateral ligaments of the ankle are common injuries in sports and active life. The cause of ankle injuries is often insufficient strength and a lack of proprioception. Proprioception is a sense of joint position. Conventional rehabilitation exercises include strengthening the muscles that control position of the ankle and manipulating the ankle to teach the patient better awareness of joint position.

An ankle elastic band in a figure eight shape has conventionally been used for ankle rehabilitation. Patients place both feet through the holes of the band. When the patient moves their feet, the elastic supplies a resistive force to exercise the muscles that control the ankle.

Other conventional devices have been used for increasing strength and proprioception of the ankle. A pair of cylinder or half-cylinder foam rollers have been used to provide an unstable surface beneath the patient's feet. The patient balances on the roller to provide awareness of the ankle position. One example of such a device is a Biofoam Roller produced by Perform Better.

Another conventional device for increasing proprioception is a wobble board. Wobble boards are circular-shaped discs of wood or plastic with a hemispherical pivot in the center under the disc. Patients perform several exercises by putting either one foot or both feet on the board. By shifting their weight, patients can make the board tilt. Rehabilitation exercises include tilting the board from side to side or back to front and making the disc's edge touch the ground in a circular pattern. The exercises strengthen ankle muscles, improve balance and proprioception. An example is the wobble board produced by Kinetic Health Corporation.

U.S. Pat. No. 5,402,800 describes an ankle laxity measurement system in which a foot clamp is attached to a patient's foot. A reference point is established on the patient's tibia. Motion between the foot clamp and the reference point is measured in six degrees of freedom with six potentiometers or a transducer system. A separate device applies force to the foot clamp in inversion-eversion and anterior-posterior directions. Signals of the forces and six degree of freedom movement are interfaced to a computer to compute, record and display the measured motions and forces. The ankle laxity measurement can be used to diagnose a ligament injury and detect if there is an instability in the ankle once the ligament has healed.

U.S. Pat. No. 4,605,220 describes an ankle exerciser for strengthening healthy ankles and rehabilitating injured ankles. The exerciser includes a foot plate attached by a universal swivel joint to a support post. The foot plate can tilt or pivot about the longitudinal and transverse axes.

U.S. Pat. No. 5,413,543 describes a portable exercising apparatus. A lower stationary platform is attached to an upper mobile platform with a spring. The upper platform can move up and down or in a radial motion. A hand and forearm exercising strap is attached to the lower platform to allow pressure to be maintained on the foot.

Rehabilitation of body parts in a virtual environment has been described. U.S. Pat. No. 5,429,140, issued to one of the inventors of the present disclosure teaches applying force feedback to hand and other articulated joints in response to a user manipulating a virtual object. In addition, U.S. Pat. No. 5,577,981 discloses a computer controlled exercise machine providing virtual reality exercise regimens to the user. The positions of a user's feet are provided with two positioning sensing arrays of cables, spools and potentiometers. The arrays are attached to the lateral sides of the user's shoes to determine the length of stride and frequency.

It is desirable to provide an ankle rehabilitation system for providing position measurements and force feedback in six degrees of freedom of the ankle which system can include a virtual reality environment.

SUMMARY OF THE INVENTION

The invention relates to a method and system for rehabilitating ankle injuries. The system includes a rehabilitation device formed of a mobile platform coupled to a fixed platform. The mobile platform is coupled to a user's foot. The position and orientation of the mobile platform is measured in relation to the fixed platform in six degrees of freedom. The force exerted by the foot against the mobile platform is measured in six degrees of freedom. The measured position and measured force are forwarded to an electronic interface and fed to a programmable computer. The programmable computer determines desired force feedback to be applied by the controller interface to the mobile platform. The desired feedback signal moves the mobile platform to a desired position or applies a desired force or torque to the mobile platform.

A linear actuator assembly can be used to couple the mobile platform and the fixed platform and provide the position and force measurements. The linear actuator assembly can be formed of a piston and position sensor. Preferably, six linear actuator assemblies are used in which each assembly measures one of the six degrees of freedom of the mobile platform.

The programmable computer can also provide a virtual reality three-dimensional graphic simulation of exercises to simulate foot or leg movement, thereby providing visual feedback to the user. For example, the virtual reality simulation can include exercises for balance, flexibility and strength. A database of user information can be used in generating the virtual reality simulation. A remote connection can be provided from the computer to a physical therapist at a remote location for storing user (patient) information remotely and transferring the information to the computer.

While patients exercise, their foot position, orientation, and output forces can become the inputs and outputs of a virtual world being simulated on the host computer. These interactive simulations make exercising both more enjoyable and effective. Through fun, game-like simulations, patients will be more likely to perform their exercises more often.

In an alternate embodiment, a rehabilitation device is coupled to each of the user's feet. A virtual reality simulation of a balance exercise with the two platforms determines force feedback to be applied to the two platforms to move the platforms to a position represented by the virtual image.

A telerehabilitation system can be formed of a pair of rehabilitation devices with a first device at a therapist location and a second device coupled to the user's foot. The therapist moves the first device to a desired position or applies desired forces to the first device. The desired positions and desired forces are transferred to the second device for applying force feedback to the second device according to the therapist's instructions.

The invention will be more fully described by reference to the following drawings.

BRIEF DESCRIPTION OF THE FIGURES

FIG. 14B is a schematic diagram of the rehabilitation system for the embodiment shown in FIG. 14A.

DETAILED DESCRIPTION

Figure 1:
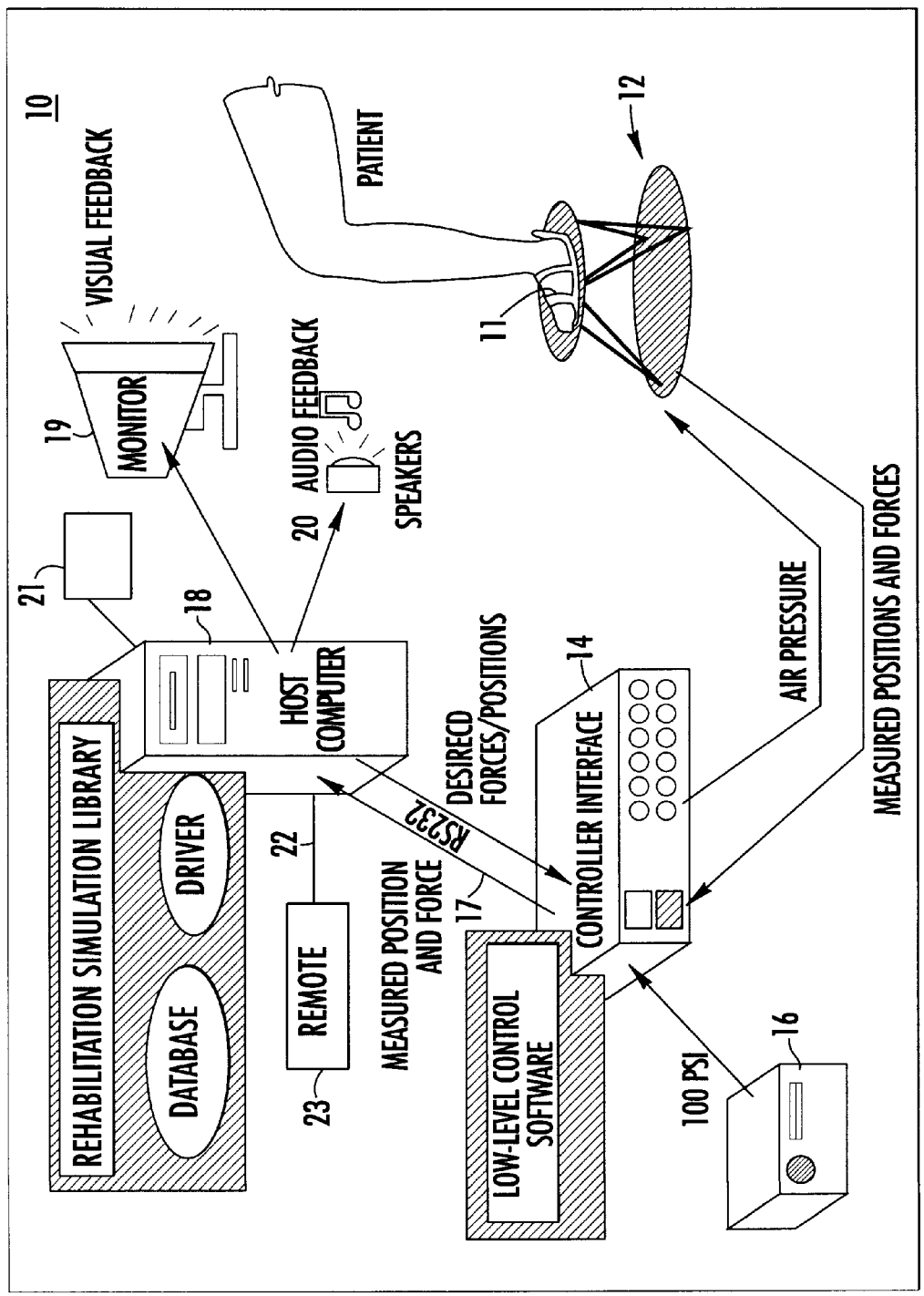
FIG. 1 is a schematic diagram of an ankle rehabilitation system in accordance with the teachings of the present invention.

FIG. 1 is a schematic diagram of an ankle rehabilitation system 10 in accordance with the teachings of the present invention. Foot 11 is coupled to rehabilitation device 12. Rehabilitation device 12 provides measurement of the position and forces applied in six degrees of freedom by foot 11 and provides force and position feedback to foot 11 in six degrees of freedom, as described in more detail below. Ankle rehabilitation system 10 can be used for strengthening the muscles that control the position of the ankle and for manipulating the ankle to teach proprioception.

Controller interface 14 connects compressor 16 to rehabilitation device 12. Compressor 16 provides air pressure for mechanically applying force feedback to rehabilitation device 12. Controller interface 14 can be part of rehabilitation device 12 or a stand alone electronic box or personal computer. Controller interface 14 also connects rehabilitation device 12 to host computer 18 over connection 17. For example, connection 17 can be a RS232 connection.

Measured positions and forces applied by foot 11 by rehabilitation device 12 are received at controller interface 14. The received measured positions and forces are electronically forwarded from controller interface 14 to host computer 18 over connection 17. Rehabilitation instructions are electronically forwarded from host computer 18 over connection 17 to controller interface 14. For example, rehabilitation instructions can include a desired position of rehabilitation device 12 or desired forces to be applied by rehabilitation device 12 on foot 11.

Display 19 is connected to host computer 18 for providing visual feedback to a user of rehabilitation device 12. Speakers 20 are connected to host computer 18 for providing audio feedback to a user of rehabilitation device 12. Host computer 18 can be coupled to hard copy device 21 for producing a hard copy of measured position and force data and rehabilitation instructions or rehabilitation progress reports. Host computer 18 can be coupled over network 22 to remote computer 23. For example, remote computer 23 can be used at a medical specialist location for receiving diagnostic or exercise information from rehabilitation device 12 and communicating rehabilitation instructions to host computer 18.

Figure 2A:
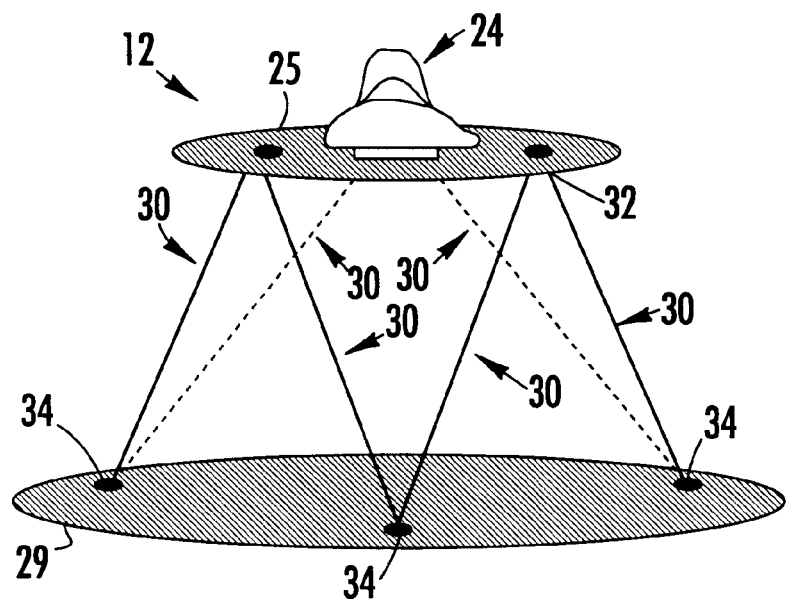
FIG. 2A is a front elevational view of a rehabilitation device used in the ankle rehabilitation system.
Figure 2B:
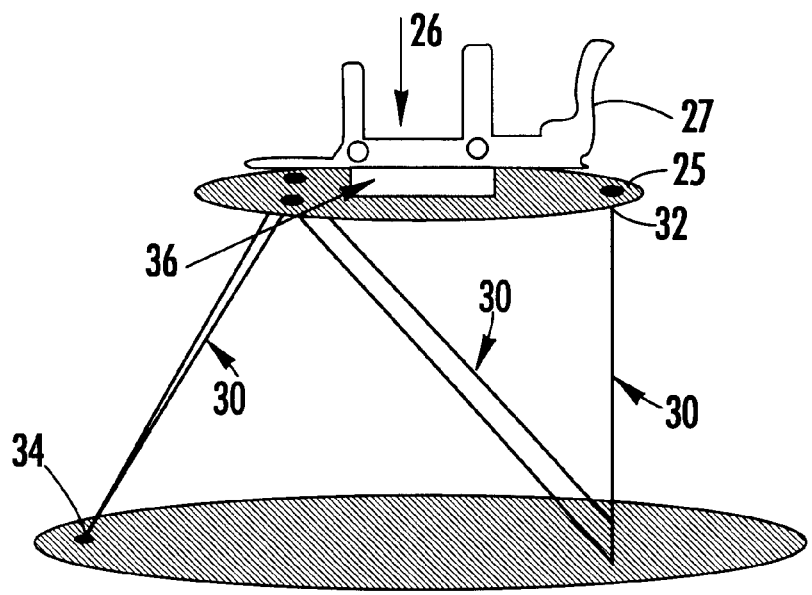
FIG. 2B is a side elevational view of the rehabilitation device.

FIGS. 2A–2D illustrate a rehabilitation device 12 comprising mobile platform 25 and fixed platform 29. Foot attachment 24 receives foot 11 for coupling foot 11 to mobile platform 25. Foot attachment 24 comprises foot harness 26 and heel support 27 attached or integral to upper platform 25, as shown in FIG. 2B.

Rehabilitation device 12 includes linear actuator assemblies 30 to connect mobile platform 25 to fixed platform 29 and allow mobile platform 25 to move relative to fixed platform 29 which remains stationary. For example, fixed platform can be screwed into a floor surface or have sufficient weight to remain stationary. Linear actuator assemblies 30 include upper attachment end 32 attached to mobile platform 25 and lower attachment end 34 attached to fixed platform 29. Mobile platform 25 and fixed platform 29 can be formed of a circular sheet of a carbon-fiber material such as Garolite. Preferably, the radius of fixed platform 29 is larger than the radius of mobile platform 25 for providing stability of rehabilitation device 12. For example, fixed platform 29 can have a 8.5 inch radius and mobile platform 25 can have a 5.25 inch radius. Alternatively, mobile platform 25 and fixed platform 29 can have a rectangular or square shape or various shapes in accordance with the teachings of the present invention.

Figure 2C:
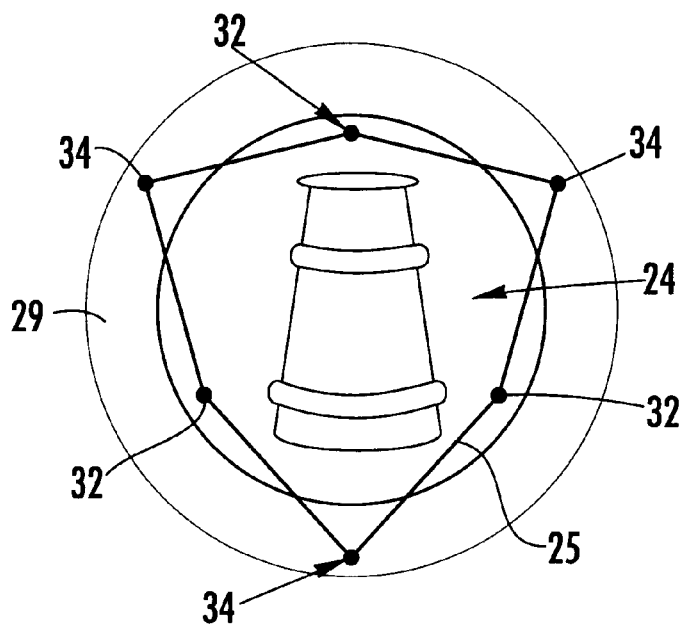
FIG. 2C is a top view of the rehabilitation device.

In a preferred embodiment, six linear actuator assemblies 30 are attached between mobile platform 25 and fixed platform 29 with each pair of linear actuator assemblies mounted in a V-shaped configuration, as shown in FIG. 2C. Accordingly, the six linear actuator assemblies 30 are attached between mobile platform 25 and fixed platform 29 with triangles rotated 120° from each other to form a six-sided star, as shown in FIG. 2C. In this embodiment, two linear actuator assemblies 30 are attached to mobile platform 25 at each corner of each triangular guide. When viewed from above in the "home" position, rehabilitation device 12 is radially symmetrical, and no linear actuator assemblies 30 enter the volume directly below the top triangle. It will be appreciated that the number and arrangement of linear actuator assemblies can be varied within the scope of the teachings of the present invention.

Figure 2D:
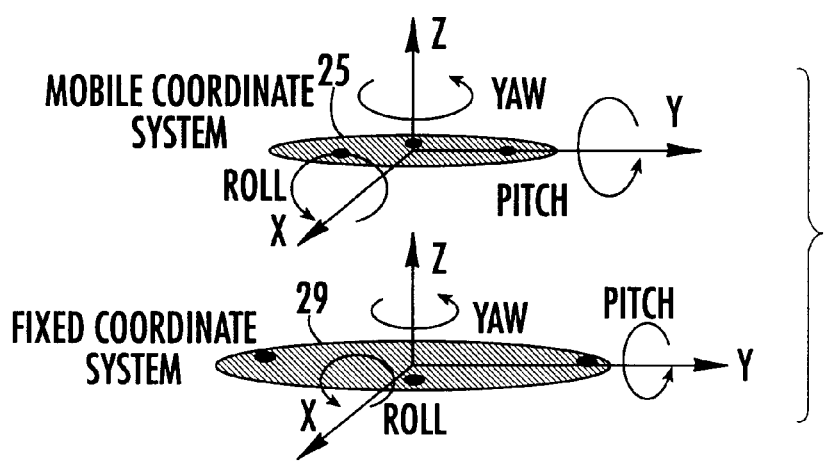
FIG. 2D is a schematic diagram of the coordinate systems used in the rehabilitation device.

As shown in FIG. 2D, the use of six linear potentiometers provides measurements in six degrees of freedom of the position (x, y, z) and orientation roll, pitch, and yaw of upper platform 25 to lower platform 29 which measurements will be generally referenced in this disclosure as the measured position.

Figure 3A:
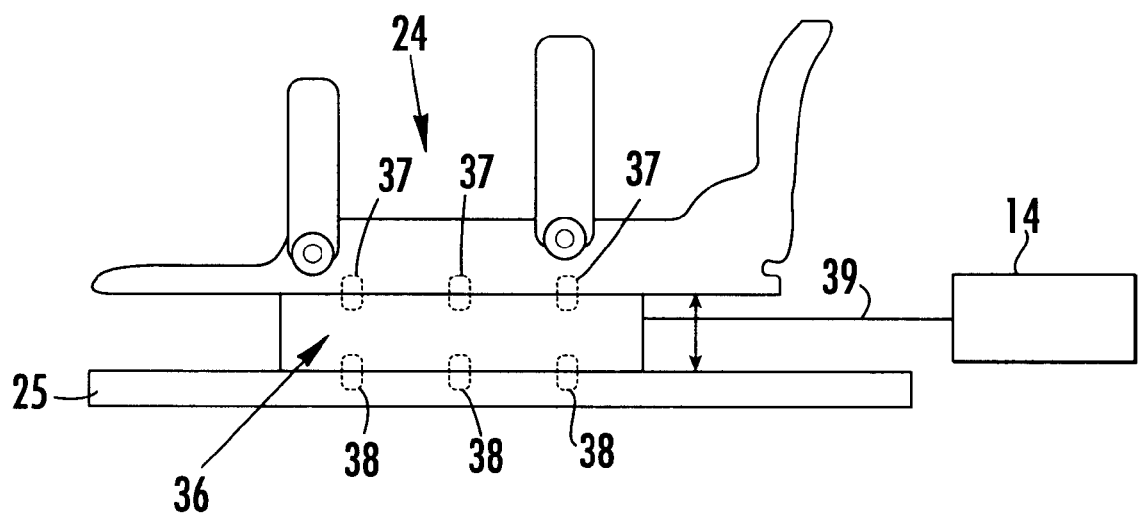
FIG. 3A is a side view of a foot attachment used in the rehabilitation device.
Figure 3B:
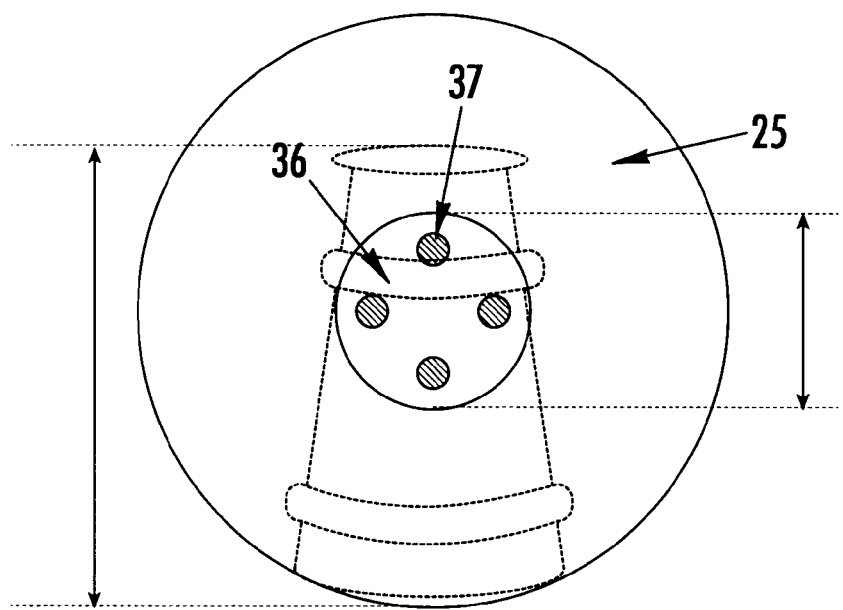
FIG. 3B is a top perspective view of the foot attachment used in the rehabilitation device.

FIGS. 3A and 3B illustrate a detailed view of the connection of foot attachment 24 to mobile platform 25 in rehabilitation device 12. Force sensor 36 is positioned between foot attachment 24 and mobile platform 25. Force sensor 36 measures in real time forces applied from foot 11 to mobile platform 25. Preferably, force sensor 36 measures forces applied in six degrees of freedom from foot 11 to mobile platform 25 to generate force measurement data 39. For example, force sensor 36 can be a six degree of freedom force sensor manufactured by JR3 Inc. as 45E15. Mounting screws 37 attach foot attachment 24 to force sensor 36. Mounting screws 38 attach mobile platform 25 to force sensor 36. Force sensor 36 provides force measurement data 39 to controller interface 14.

Figure 4:
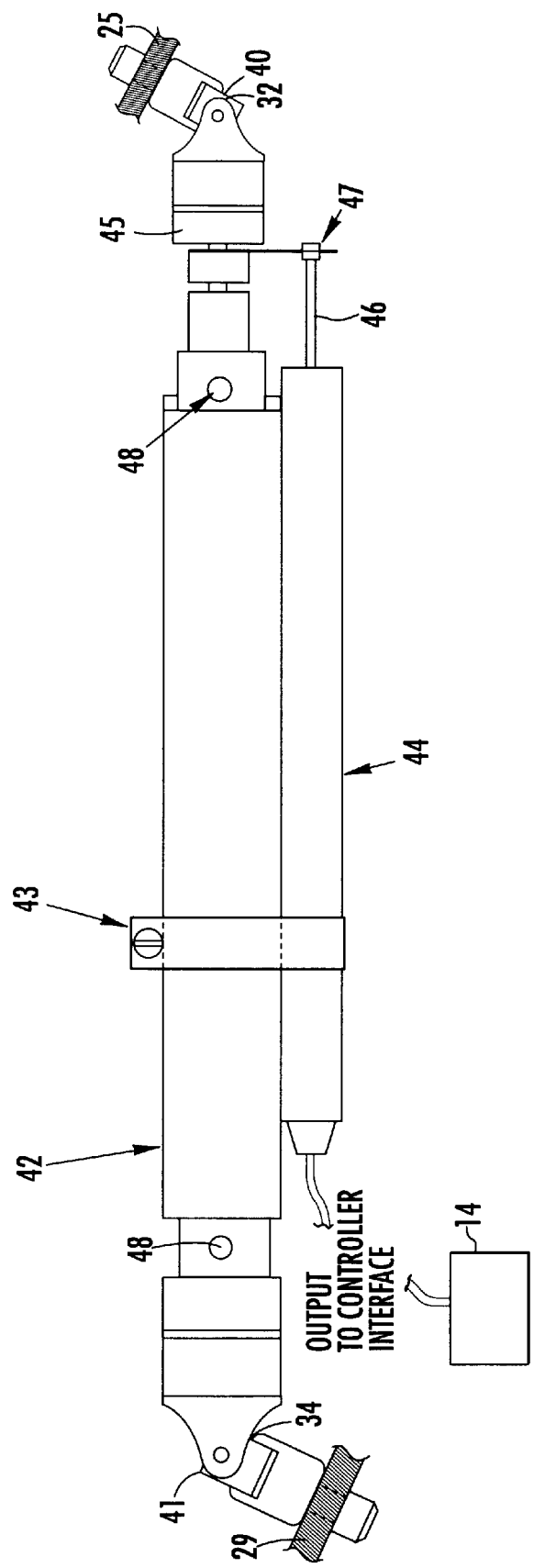
FIG. 4 is a schematic diagram of a linear actuator assembly used in the rehabilitation device.

FIG. 4 is a schematic diagram of linear actuator assembly 30. Upper joint 40 connects upper attachment end 32 to mobile platform 25. Lower joint 41 connects lower attachment end 34 to fixed platform 29. For example, upper joint 40 and lower joint 41 can be universal joints. Piston 42 is mounted in parallel with position sensor 44. Lower actuator attachment 43 couples piston 42 to position sensor 44. For example, lower actuator attachment 43 can be a metal band and screw assembly. Piston rod 45 extends from piston 42. Sensor rod 46 extends from position sensor 44. Piston rod 45 and sensor rod 46 move within upper actuator attachment 47. Sensor rod 46 moves with piston rod 45 for indicating the position of piston rod 45. Lower actuator attachment 43 and upper actuator attachment 47 ensure that position sensor 44 is coupled to piston 42.

Preferably piston 42 is an air piston which is coupled with air tubes 48 to controller interface 14. Piston rod 45 is extended and retracted by applying respective air pressures to air tubing 48 to change the length of piston 42, thereby changing the position of mobile platform 25 in relation to fixed platform 29. Air pressure is also applied through air tubes 48 to piston 42 to apply force feedback from linear actuator assembly 30 to mobile platform 25, thereby applying translation forces and torques to foot 11.

Preferably, piston 42 can be formed of glass or graphite. For example, piston 42 can be a double acting piston having a pair of air compartments as manufactured by Airport Corporation as Airpel E16D4.OU. The Airpel piston has a maximum force output of 137.34 N and a friction of 1% to 2% of the load to yield a dynamic range of between about 50 and about 100.

Preferably, position sensor 44 is a linear potentimeter that changes resistance with the movement of sensor rod 46 to provide position measurements of piston 42. For example, position sensor 44 can be a linear resitive transducer manufactured by Data Instruments as XDCR MLT. Position sensor 44 is connected to controller interface 14. Position measurement data 49 from position sensor 44 relating to the measured position of piston 42 is read by controller interface 14.

Figure 5:
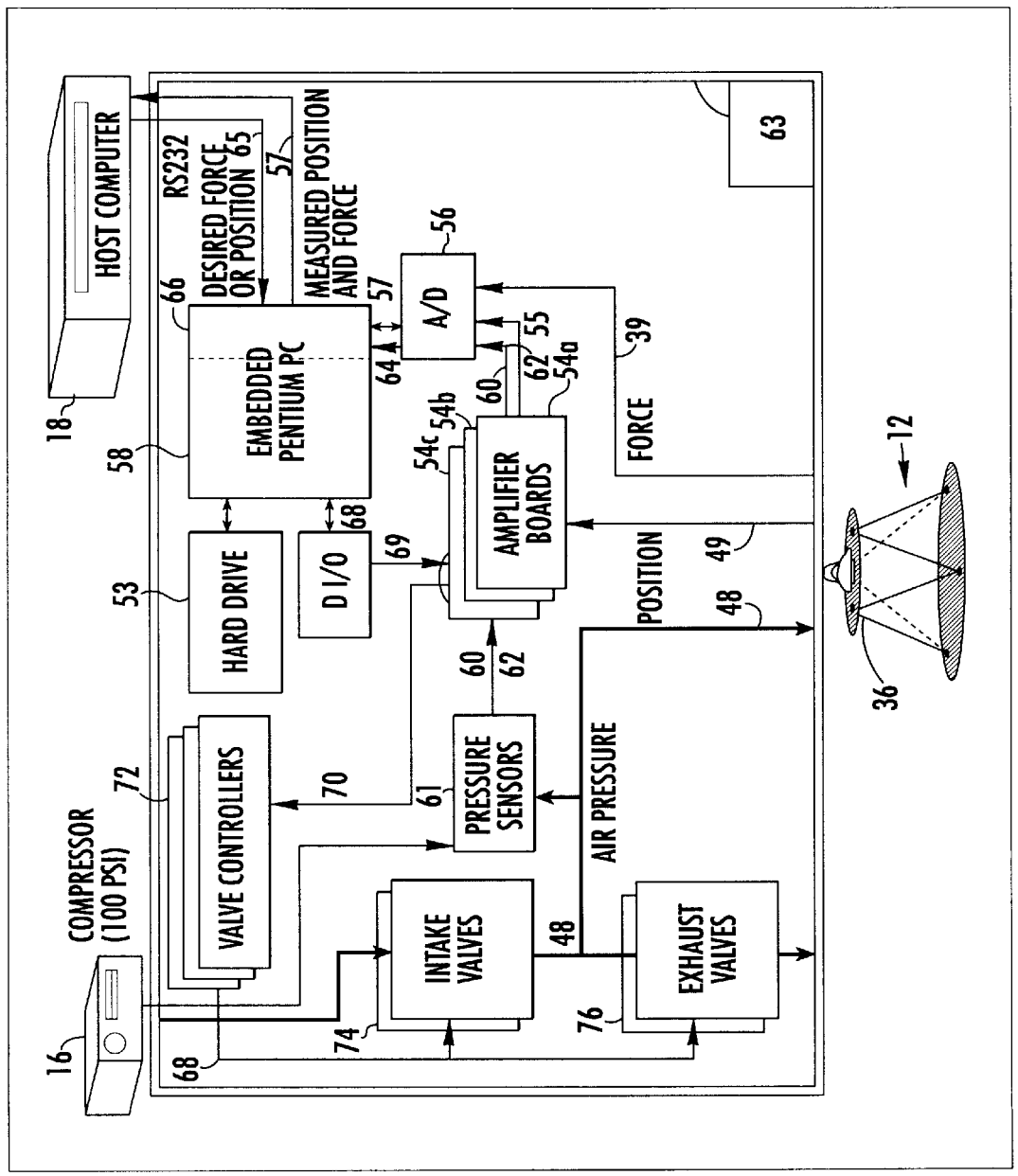
FIG. 5 is a block diagram of a controller interface used in the ankle rehabilitation system.

FIG. 5 illustrates a block diagram of controller interface 14. Controller interface 14 receives position measurement data 49 and force measurement data 39 from rehabilitation device 12. Preferably, position measurement data 49 is six analog signals, respectively, from each of the preferred six position sensors 44 of six linear actuator assemblies 30, for providing position measurements one for each of the six degrees of freedom of foot 11. Force measurement data 39 is generated from force sensor 36. Preferably, force sensor 36 provides six signals one for each of the six forces or torques of foot 11.

Amplifier board assembly 54 buffers position measurement data 49. Amplifier board assembly 54 includes buffer boards 54a, 54b and 54c. Buffered position and force data 55 from amplifier board assembly 54 is applied to analog to digital converter 56 to convert buffered position and force data 55 into a binary number. Position and force output 57 from analog to digital converter 56 is received at personal computer board 58. For example, personal computer board 58 can be a Pentium embedded PC board. Hard drive 53 can be coupled to personal computer board 58 for providing a storage medium. Position and force output 57 from personal computer board 58 is transmitted to host computer 18.

Pressure sensors 61 interface piston 42 of rehabilitation device 12 to generate piston pressure measurement data 60 from each compartment of piston 42. In a double acting air piston having two air compartments, one pressure sensor 61 is coupled to each air compartment to provide two pressure measurements, one for each air compartment. In the preferred embodiment, controller interface 14 receives twelve pressure measurements in which two pressure measurements are received from each of the six preferred linear actuator assemblies 30.

Pressure sensor 61 is also coupled to compressor 16 to sense compressor pressure measurement data 62 of air pressure in compressor 16. For example, the air pressure can be about 100 psi. Piston pressure measurement data 60 and compressor pressure measurement data 62 are buffered by amplifier board assembly 54 and applied to analog to digital converter 56 before being sent to interface software module 66 of personal computer board 58 as sensor output 64. Power supply unit 63 provides power to controller interface 14.

Host computer 18 determines desired force and position measurement data 65 for rehabilitation device 12. Desired force and position measurement data 65 is applied to interface software module 66. Interface software module 66 determines, from sensor output 64 and desired force and position measurement data 65, the pressure to be applied to each piston 42 for providing desired force feedback and position of rehabilitation device 12. Preferably, host computer 18 continually transmits desired force and position measurement data 65 for controlling rehabilitation device 12. Interface software module 66 is typically implemented by personal computer board 58 to determine the pressure to be applied to each piston 42 for providing force feedback and position of rehabilitation device 12. Alternatively, some or all of the functions of interface software module 66 can be implemented by host computer 18.

Interface software module 66 also includes low-level control functions for receiving input and generating output from controller interface 14. In the preferred embodiment, input to low-level control of controller interface 14 includes twelve pressure values as the pressure in each of pistons 42 which are dual pistons, six translation values as the length of each of pistons 42, one desired force or desired position from host computer 18 and six force values from force sensor 36. Output from low-level control of controller interface 14 in the preferred embodiment include twenty four valve control signals for controlling pressure in each of pistons 42 which are dual pistons, six force values from force sensor 36 and six translation values of the displacement of the length of each of six pistons 42.

Valve control signal 68 is generated by interface software module 66 to specify whether a valve should be open or closed based on desired force and position measurement data 65. Digital input/output 69 applies valve control signal 68 to amplifier board assembly 54. Amplified valve control signal 70 is applied to valve controllers 72. Valve controllers 72 interface intake valves 74 and exhaust valves 76 for opening and closing intake valves 74 and exhaust valves 76, thereby increasing or decreasing the pressure in respective pistons 42, as described in more detail below. In the preferred embodiment, a valve control signal 68 is provided for each of twelve intake valves 74 and twelve exhaust valves 76 which are used to control six pistons 42 which are dual acting pistons having double air intake compartments. Air tubing 48 connects intake valves 74 and exhaust valves 76 to pressure sensors 61, air compressor 16 and rehabilitation device 12.

Figure 6A:
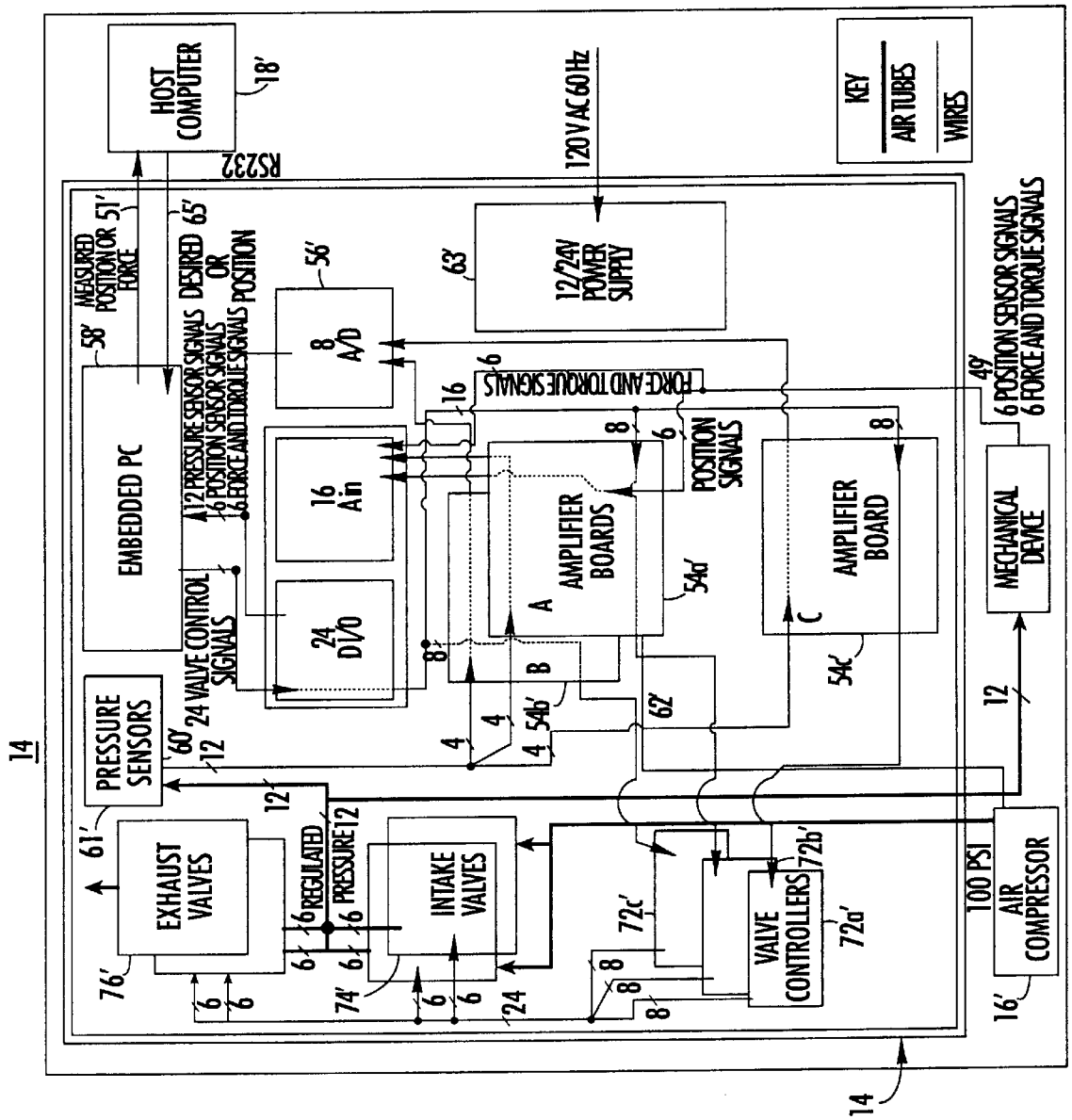
FIG. 6A is a schematic diagram of the controller interface.
Figure 6B:
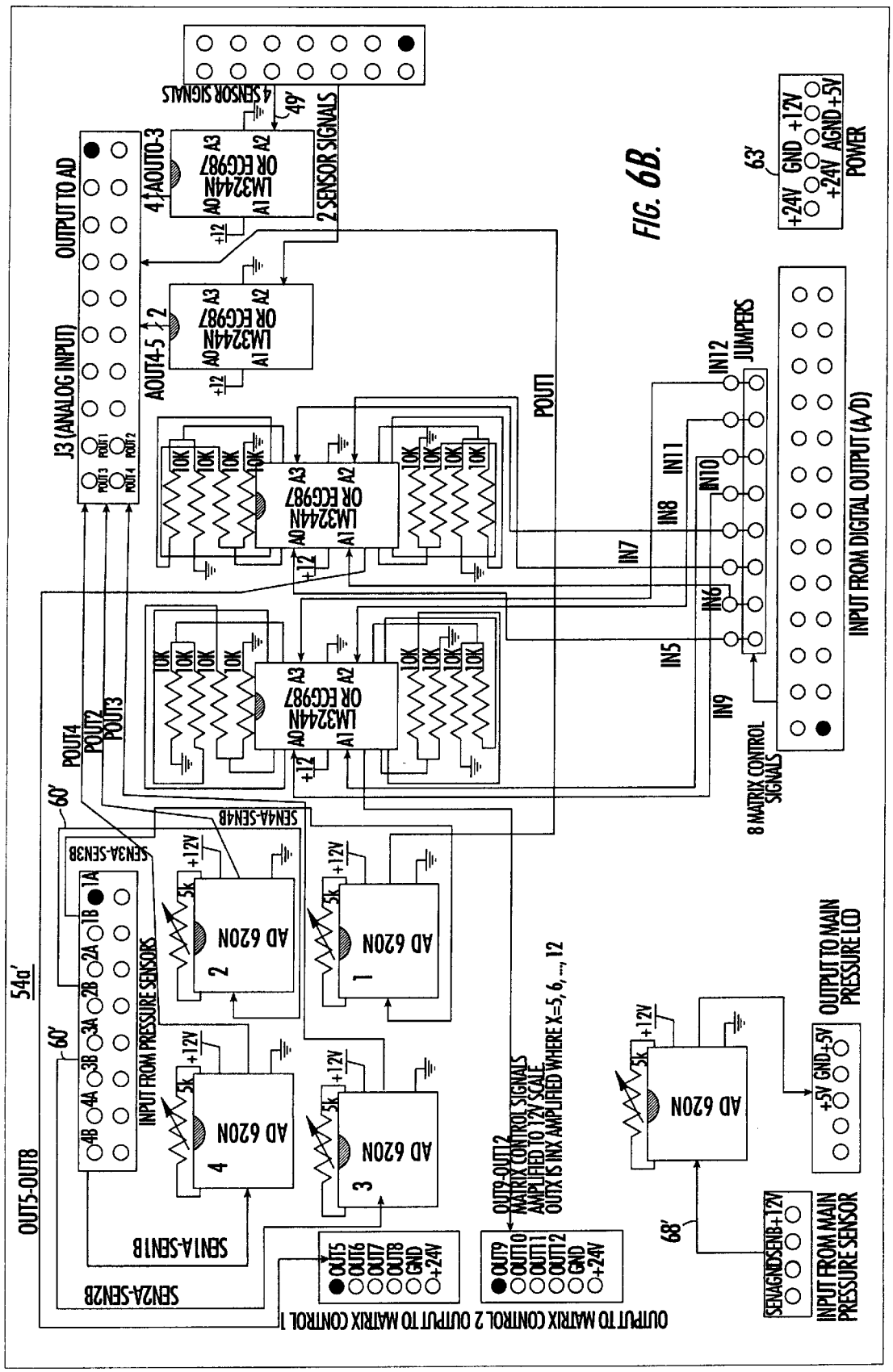
FIG. 6B is a schematic diagram of an amplifier board used in the controller interface.
Figure 6C:
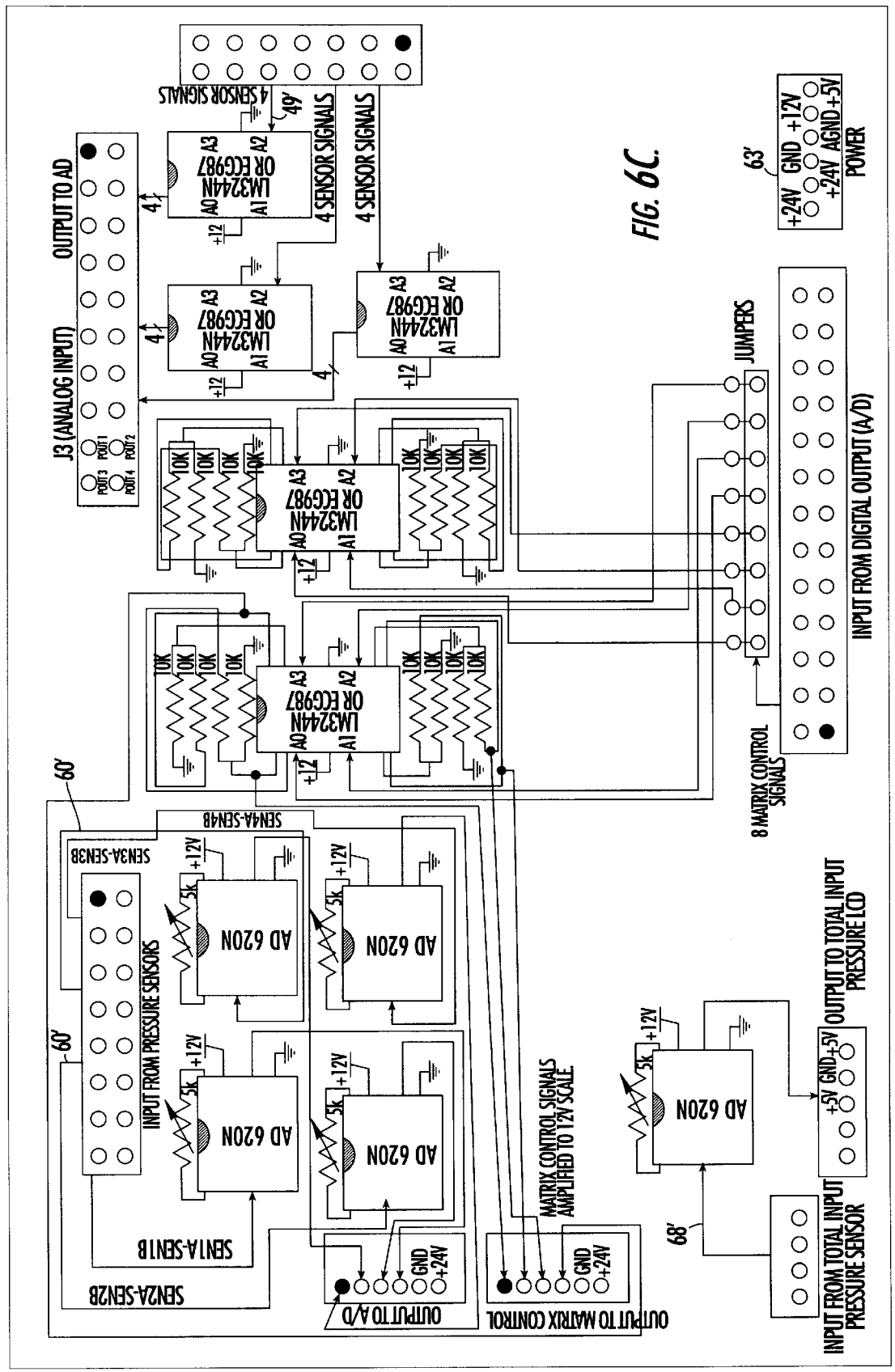
FIG. 6C is a schematic diagram of additional amplifier boards used in the controller interface.
Figure 6D:
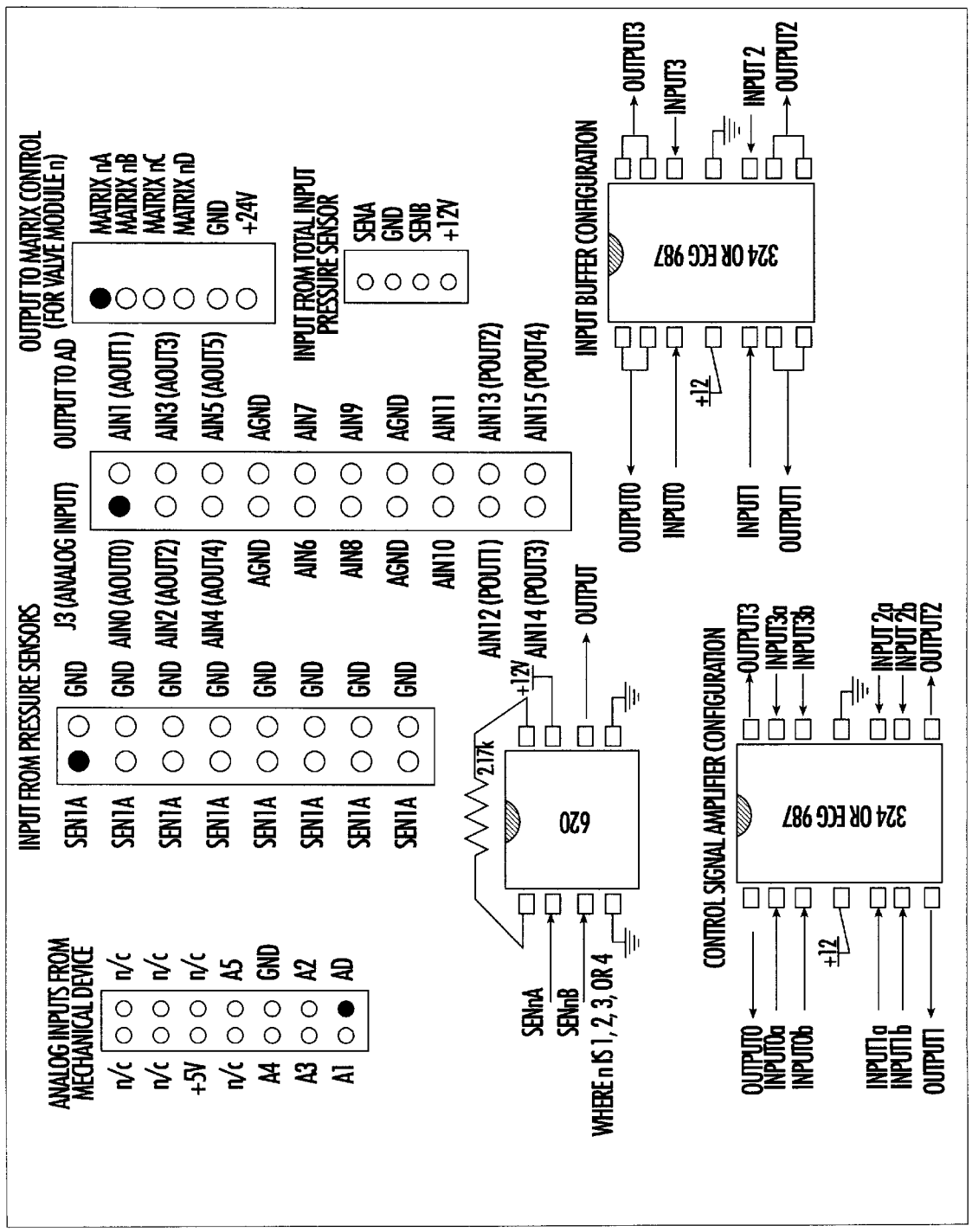
FIG. 6D is a schematic diagram of amplifier board connectors.

FIGS. 6A–6F illustrate more detailed schematic diagrams of controller interface 14 and portions thereof for a preferred embodiment including six linear actuator assemblies 30 (which are shown in block diagram form in FIG. 5). Components in the schematic will be accorded the same reference character followed by an (') as their corresponding components in the block diagram. FIG. 6A illustrates a schematic electrical and pneumatic diagram of controller interface 14. FIG. 6B illustrates a schematic circuit diagram for amplifier buffer board 54a'. FIG. 6C illustrates a schematic circuit diagram for amplifier boards 54b' and 54c'. FIG. 6D illustrates buffer board connector and IC pins.

Position measurement data 49' comprising six position signals are buffered by a chip designated as LM324N op amp chip distributed by Newark Electronics on amplifier board 54a'. The buffered data is converted to a binary number by an analog to digital converter and sent to the personal computer board, shown in the block diagram in FIG. 5.

Piston pressure measurement data 60' related to measurements of pressures in each of the twelve compartments of the six double-acting pistons is fed to buffer amplifier board assembly 54 for buffering and amplification by chips designated AD620N, which are available from Newark Electronics and are located on all three amplifier boards 54a', 54b' and 54c'. The buffered data is converted to a binary number by an analog to digital converter and sent to the personal computer board, shown in the block diagram in FIG. 5. Compressor measurement data 62' is also amplified by one of the chips designated by AD620N on buffer board 54a'.

Preferably, personal computer board 58' outputs a control signal for each of the twenty-four pressure valves of the preferred embodiment. The signals are output as digital signals by analog digital converter 56'. The signals are fed to amplifier boards 54a', 54b' and 54c' for amplification to a 12 V scale and then sent to pressure valve controller boards 72a', 72b' and 72c'. Eight signals respectively go to each of the controller boards 72a', 72b' and 72c'.

Figure 6F:
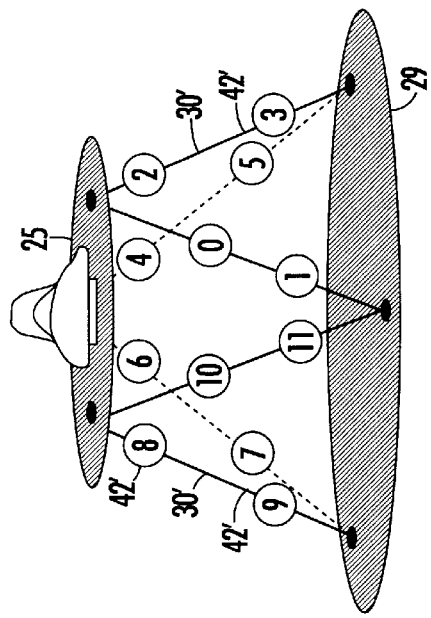
FIG. 6F is a front elevational view of the rehabilitation system including connection of intake and exhaust valves to actuator assemblies.
Figure 6E:
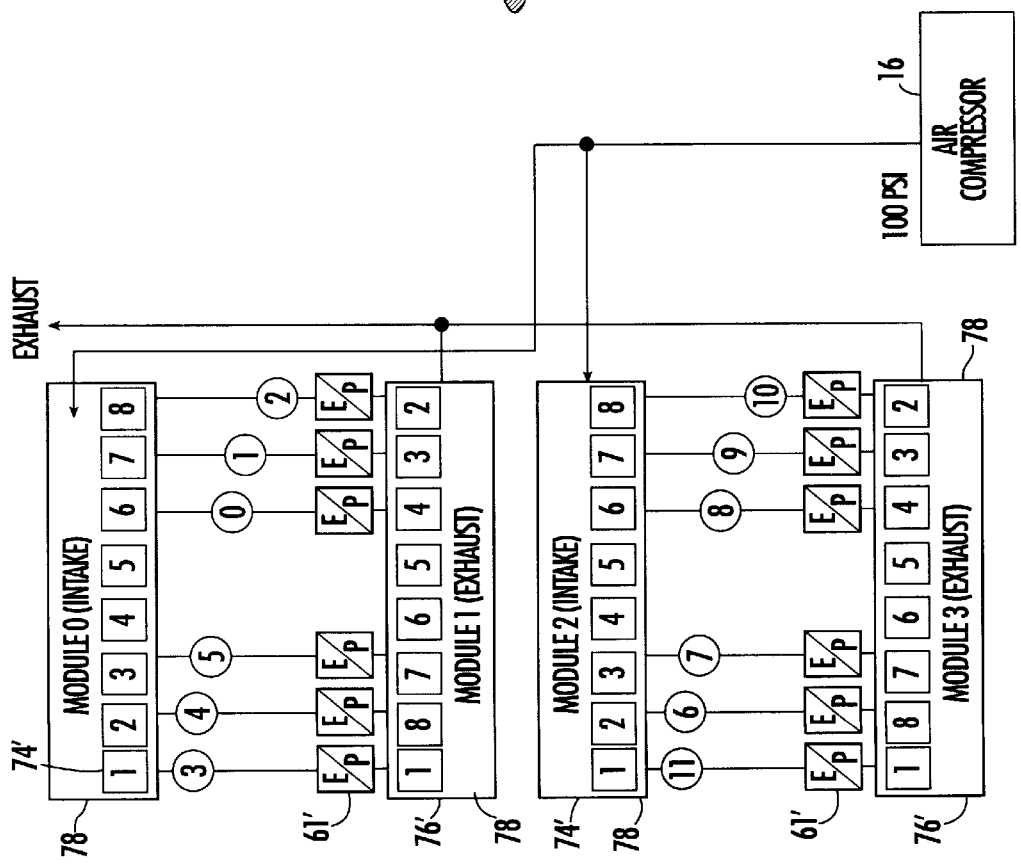
FIG. 6E is a schematic diagram of connection of intake and exhaust valves to actuator assemblies.

FIGS. 6E and 6F show connection of the preferred twelve intake valves 74' and the preferred twelve exhaust valves 76' to twelve compartments of pistons 42'. Preferably, four valve modules 78 are used for controlling intake valves 74' and exhaust valves 76'. Two valve modules 78 are used for each of eight intake valves 74' and two valve modules 78 are used for each of eight exhaust valves 76'. The valve usage is distributed evenly across the four valve modules 78 with each valve module using 6 of its 8 valves. In this embodiment, four intake valves 74' and four exhaust valves 76' are unused and always closed. For example, valve modules 78 8-input pressure valve module and 8-output pressure valve module manufactured by Matrix respectfully as MX758.8E3CKK.L and MX7588.E3CKK. It will be appreciated that a valve module having six valves can be used in accordance with the teachings of the present invention and other arrangements of valve modules, exhaust valves and intake valves are possible in accordance with the teachings of the present invention.

Two sets of intake valves 74' and exhaust valves 76' are labeled with values from 1 to 6. Each actuator assembly 30 includes a piston 42' having two compartments. The twelve compartments of pistons 42' are labeled from 0 to 11. Each intake valve 74' is connected to an exhaust valve 76'. The pressurized air controlled by the intake valve 74' and exhaust valve 76' is sent to a connected respective compartments of piston 42'.

Figure 7:
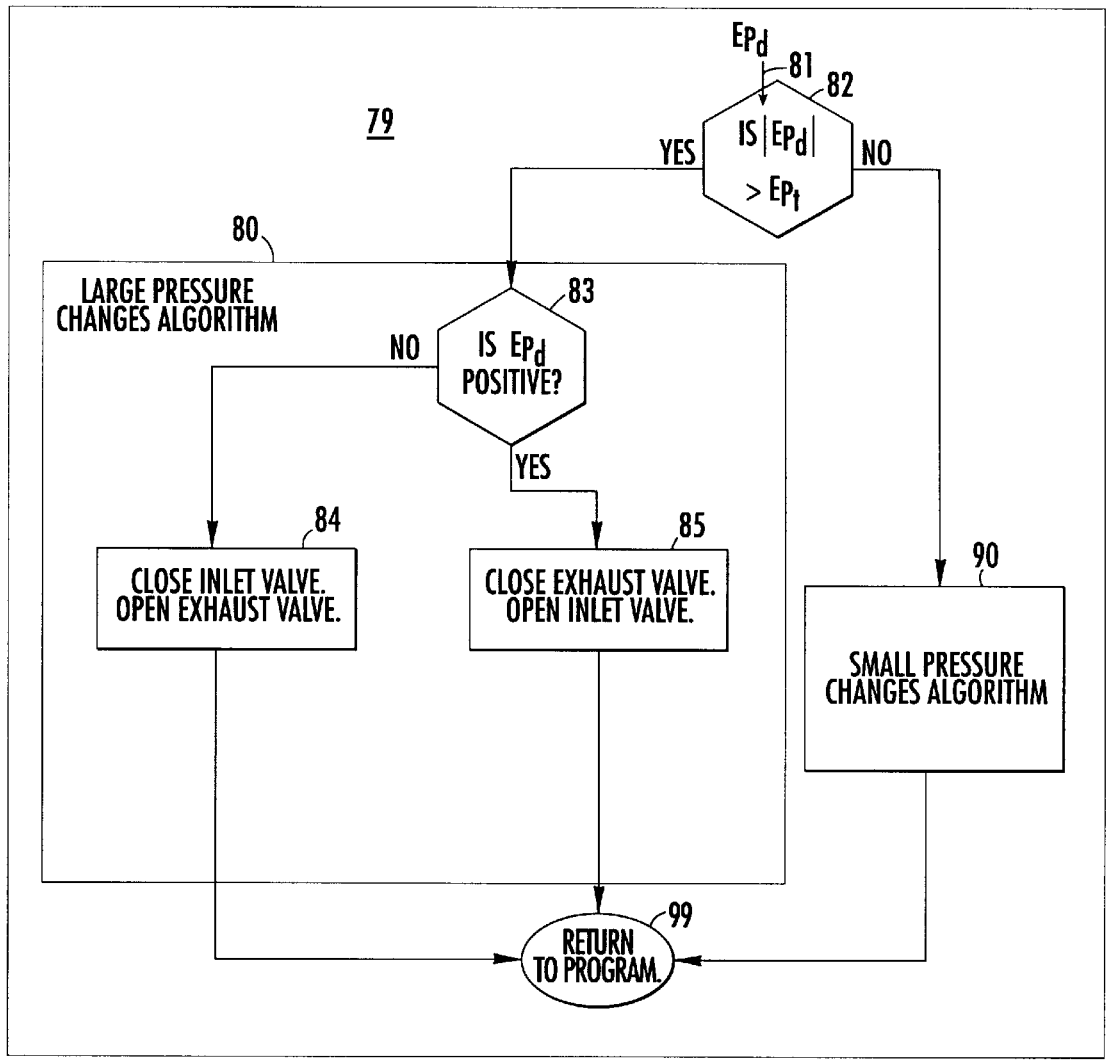
FIG. 7 is a flow diagram of a pressure control loop including a large pressure changes algorithm.
Figure 8:
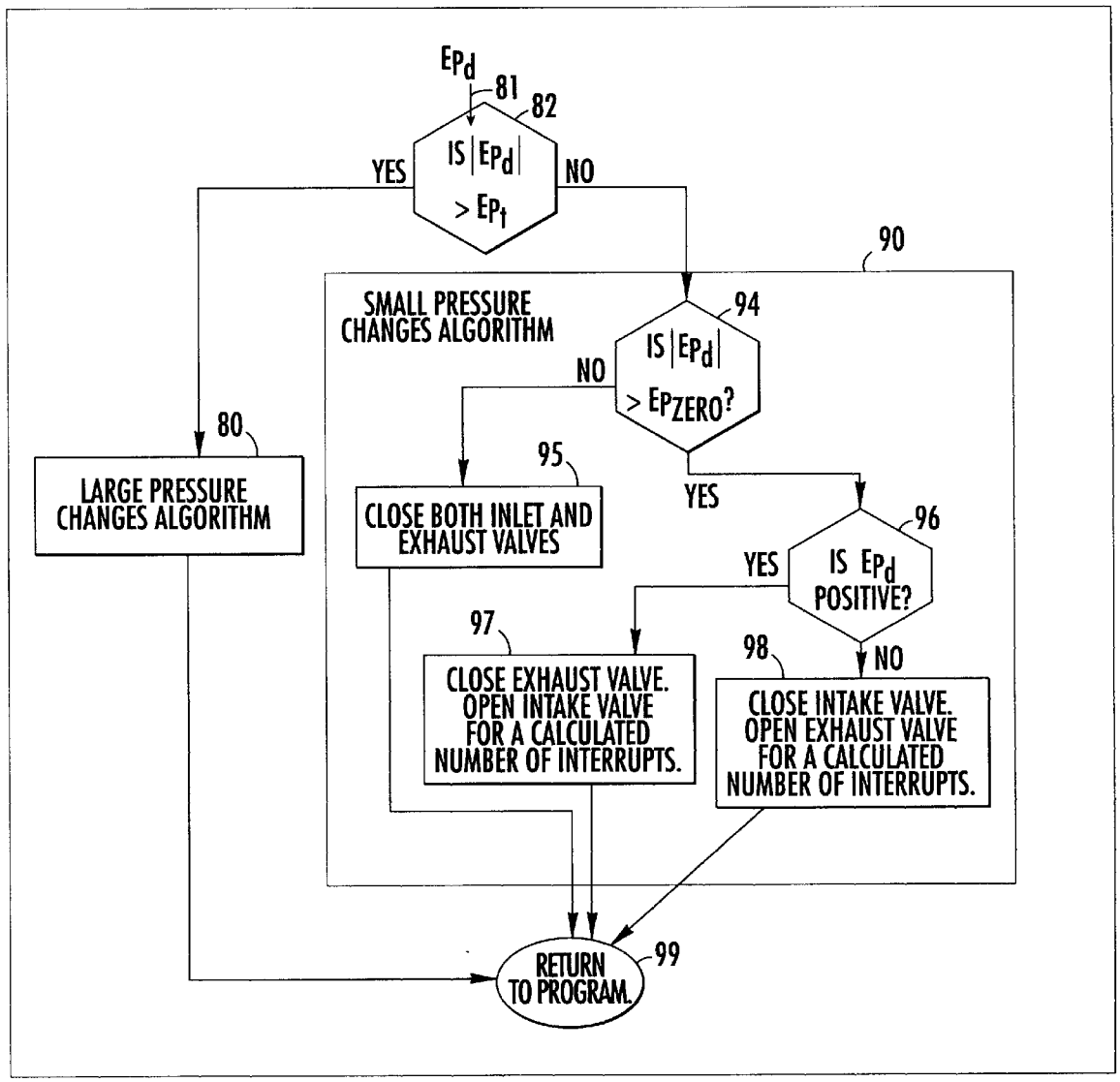
FIG. 8 is a flow diagram of a pressure control loop including a small pressure changes algorithm.

FIGS. 7 and 8 represent flow diagrams of pressure control loop 79 including large pressure changes algorithm 80 and small pressure changes algorithm 90 which can be used in interface software module 66 for controlling intake valves 74 and exhaust valves 76. Each instance of the interrupt controls one of six linear actuator assemblies, deciding whether its associated intake valve 74 and exhaust valve 76 should be open or closed. Preferably, pressure control loop 79 is an interrupt function that is executed frequently by interface software module 66, for example every five seconds. Each instance of the interrupt controls one of six linear actuator assemblies to decide whether its associated intake valve 74 and exhaust valve 76 should be open or closed. Input 81 to pressure control loop 79 represented by $EP_d$ is the change of pressure that is desired in each compartment of piston 42 of the determined linear actuator assembly 30. In block 82, it is determined if $EP_d$ is greater than $EP_t$ which represents a pressure control constant. When $EP_d$ is greater than $EP_t$, block 83 is implemented to determine if $EP_d$ is positive or negative, as shown in FIG. 7. $EP_t$ is determined experimentally.

If $EP_d$ is determined as not positive, block 84 is executed to close intake valve 74 and open exhaust valve 76 until the next interrupt that controls the determined linear actuator assembly 30, thereby decreasing pressure in the compartment of piston 42.

If $EP_d$ is determined as positive, block 85 is executed to close exhaust valve 76 and open intake valve 74 until the next interrupt that controls the determined linear actuator assembly 30, thereby increasing pressure in the compartment of piston 42.

If it is determined in block 82 that $EP_d$ is less than $EP_t$, small pressure changes algorithm 90 is executed to control slight pressure changes in compartments of piston 42, as shown in FIG. 8. In block 94, it is determined if $EP_d$ is greater than or equal to about-zero pressure, denoted $EP_{zero}$. If $EP_d$ is not greater than $EP_{zero}$, both intake valve 74 and exhaust valve 76 are closed to maintain the current pressure, in block 95.

In block 96, it is determined if $EP_d$ is positive. Block 97 is executed if $EP_d$ is positive and intake valve 74 is opened and its exhaust valve 76 is closed for a calculated number of interrupts in order to increase pressure in compartments of piston 42. If $EP_d$ is negative, block 98 is executed and exhaust valve 76 is opened and intake valve 74 for a calculated number of interrupts to decrease pressure of the compartment of piston 42. At the beginning of each interrupt, the system checks for the linear actuator assemblies 30 that have recently been controlled using the small pressure control algorithm 90 and closes their respective intake valves 74 and exhaust valves 76 as necessary. These very short durations allow slight changes in pressure that the time-based approach would not allow. It has been found that these very short durations allow slight changes in pressure to be applied to the compartments of pistons 42. After execution of either block 89 or block 86 of large pressure algorithm 80 or block 95, block 97 or block 98 of small pressure changes algorithm 90, block 99 is executed to return to interface software module 66.

Kinematic transformations are used to transform the desired location of mobile platform 25 with respect to fixed platform 29 into lengths of pistons 42 of linear actuator assemblies 30 and to transfer lengths of pistons 42 of linear actuator assemblies 30 into the location of mobile platform 25 with respect to fixed platform 29. For example, conventional techniques for inverse kinematic transformations to output the lengths of cylinders or pistons necessary to reach a desired position, such as described in J. E. Dieudonne, R. V. Parrish, & R. E. Bardusch, An Actuators Extension Transformation for a Motion Simulator and an Inverse Transformation Applying Newton-Raphson's Method, NASA, 1972 hereby incorporated by reference into this application and for forward kinematics transformations for determining the position of the platform from the length of the pistons, such as described in C. C. Nguyen & F. J. Pooran, Kinematic Analysis and Workspace Determination of a 6 DOF CKCM Robot End-Effector, Journal of Mechanical Working Technology, 1989 pp. 283–294, hereby incorporated by reference into this application, can be implemented in controller interface 14.

Figure 9A:
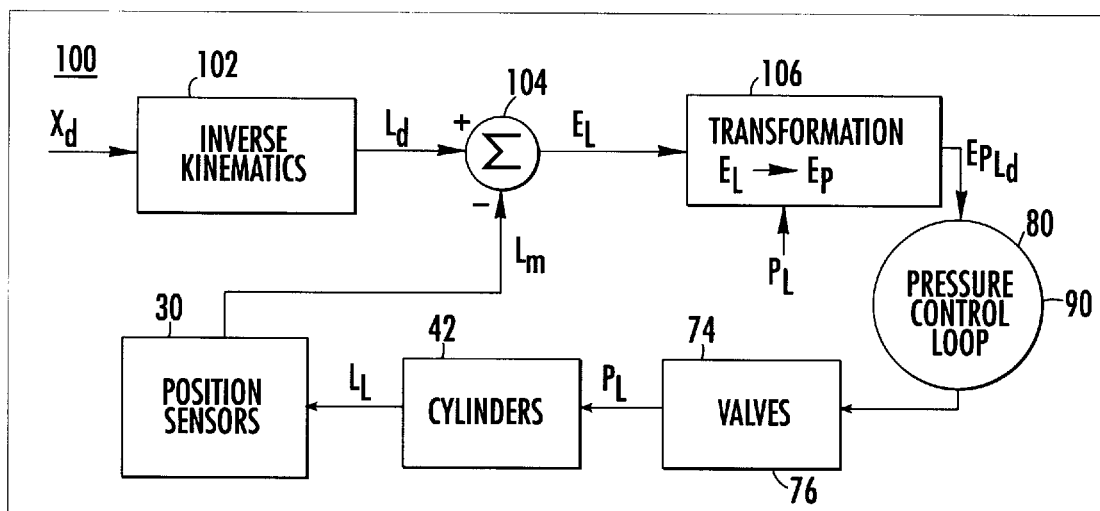
FIG. 9A is a block diagram of a position control loop.
Figure 9B:
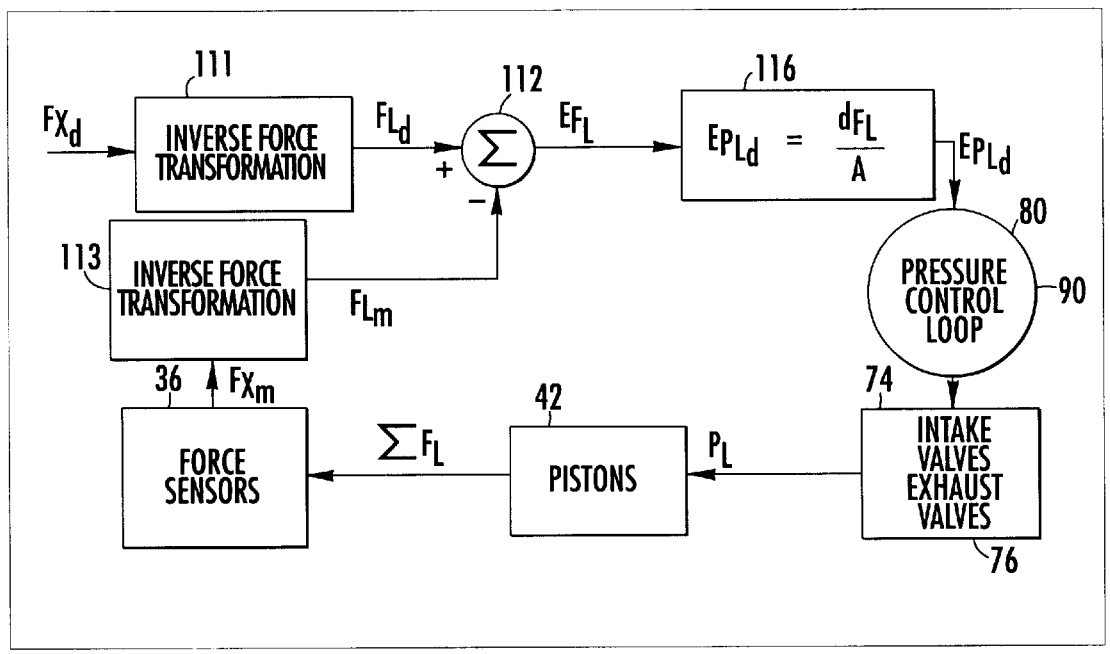
FIG. 9B is a block diagram of a pressure control loop.
Figure 9C:
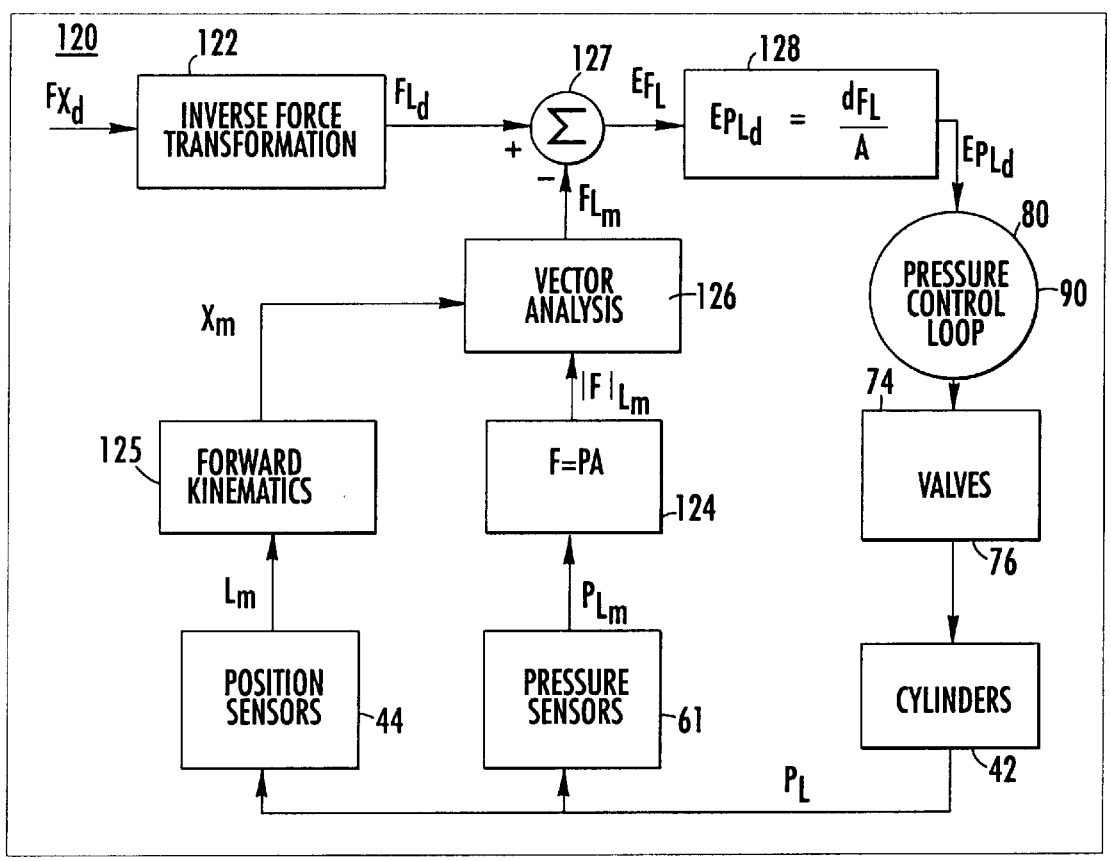
FIG. 9C is a block diagram of an alternate pressure control loop.

FIGS. 9A–9C are schematic diagrams for implementing control of rehabilitation device 12 with interface controller 14 to ensure rehabilitation device 12 is operating in conformance with instructions from host computer 18. The following definitions are used in the FIGS. 9A–9C:

L represents the length of each piston;
$P_L$ represents the pressure in each piston air compartment;
F represents a force vector;
$|F|$ represents the magnitude of the force vector;
X represents a position of upper platform 25;
A represents the area of an air compartment for a piston;
subscript d denotes desired quantities;
subscript m denotes measured quantities;
subscript L denotes that the object is related to particular pistons, for
example, $L_L$ is the length of each piston, FL is the force exerted by each
piston, and $P_L$ is the pressure in each piston; and
subscript X represents global coordinates.

FIG. 9A depicts position control loop 100 implemented by controller interface 14 to control the position of rehabilitation device 12 such that the position of rehabilitation platform 12 is the same as the position desired by host computer 18. The desired position, $x_d$, of the mobile platform 25 is inputted to control loop 100 from host computer 18. The desired length, $L_d$, of each piston 42 is determined, in block 102. In block 104, the desired length, $L_d$, is compared with the measured length, $L_m$, and is converted into a change in length, $E_L$, for each piston 42. A transformation is applied to convert the change in length $E_L$ for each piston 42 into a change in pressure, $EP_{Ld}$, for each piston 42, in block 106. This transformation ensures that the change in pressure is directly proportional to the change in length and the measured pressure in each piston 42. The change in pressure, $EP_{Ld}$, is inputted to large pressure changes algorithm 80 and small pressure changes 90 algorithm, described above, which control intake valves 74 and exhaust valves 76 to realize the desired pressure in each piston 42 represented by $P_L$ and to determine the length, $L_L$ of each piston 42.

FIG. 9B illustrates a force control loop 110 to control the force feedback to be exerted by rehabilitation device 12 such that the force exerted by rehabilitation device 12 is the same as the force desired by host computer 18. Desired force, $F_{xd}$, is applied from host computer 18 to force control loop 110. In block 111, an inverse kinematic transformation is applied to determine the desired length $F_{LD}$ of piston 42. In block 113, an inverse kinematic transformation is applied to the force $F_{XM}$ measured at force sensor 36 to determine the length of piston 42, $F_{LM}$. The change between desired length, $F_{Ld}$, and measured length, $F_{LM}$, from force sensor 36, is determined in block 112. The transformed change in force for each piston, $E_{FL}$, is then converted into a desired change in pressure, $EP_{LD}$, for each piston 42, in block 116. The change in pressure, $EP_{Ld}$, is inputted to large pressure changes algorithm 80 and small pressure changes 90 algorithm, described above, which control intake valves 74 and exhaust valves 76 to realize the desired pressure in each piston 42 represented by $P_L$ and to determine the forces, $F_L$, to be applied by pistons 42.

FIG. 9C illustrates an alternative force control loop 120 without using a measurement from force sensor 36. Desired force, $F_{xd}$, is applied from host computer 18 to inverse force transformation determined in block 122. Pressure sensors 61 input the pressure, $P_{LM}$. The magnitude of the force $|F|_{LM}$ in each piston 42 is calculated in block 124 as the force, F, is equal to the pressure, P, times the area, A, of piston 42. Position sensors 44 provide the measured length, $L_m$. In block 125, through forward kinematics, the position, $X_m$, of mobile platform 25 is determined. In block 126, the position, $X_m$, of mobile platform 25 is combined with the determined magnitude of the measured force, $|F|_{Lm}$, in vector analysis to determine the directions of the forces in each piston 42. In block 127, the difference, $E_{FL}$, between the desired force $F_{Ld}$, and the measured force, $F_{LM}$, is determined. In block 128, the desired change in each piston, $EP_{Ld}$, is determined. The change in pressure, $EP_{Ld}$, is inputted to large pressure changes algorithm 80 and small pressure changes 90 algorithm, described above, which control intake valves 74 and exhaust valves 76 to realize the desired pressure in each piston 42 represented by $P_L$. Given the description herein, those skilled in the art will know how to design and program controller interface 14.

Figure 10:
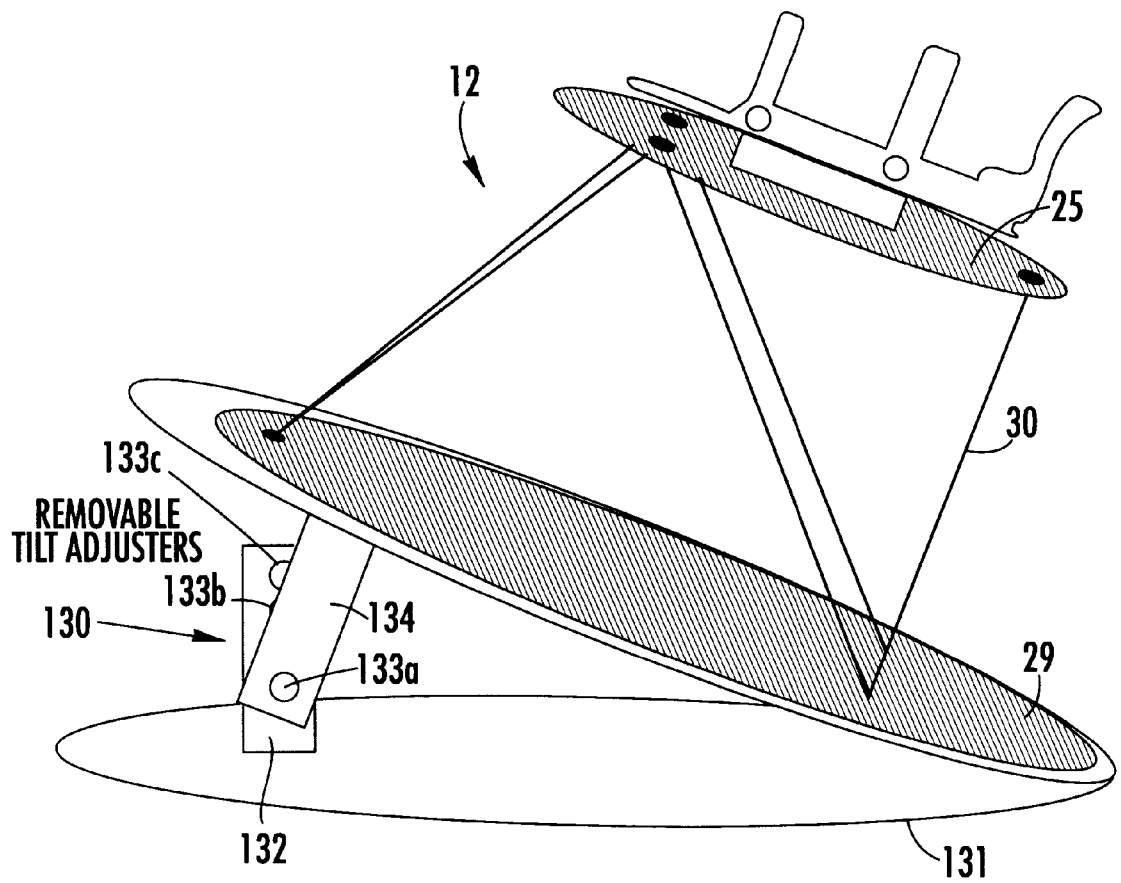
FIG. 10 is a perspective view of a tilt adjustment device used with the rehabilitation system.

FIG. 10 illustrates a perspective view of an alternative embodiment including tilt adjustment device 130 positioned between fixed platform 29 and floor support 131. Tilt adjustment device adjusts the angle $A_p$ between fixed platform 29 and floor support 131, thereby flexing foot 11 if a user of rehabilitation device 12 maintains their leg in a substantially vertical position. Support 132 extends from floor support 131. Support 132 includes a plurality of apertures 133a, 133b and 133c. Fixed platform 29 support 134 extends from fixed platform 29. Fixed platform support 134 is coupled to one of apertures 133a, 133b or 133c, for example with a screw and washer arrangement, wherein depending on the aperture 133a, 133b or 133c coupled to fixed platform support 134 angle $A_p$ will be varied. Mobile platform 25 is attached to fixed platform 29 with linear actuator assemblies 30, as described above.

Figure 11:
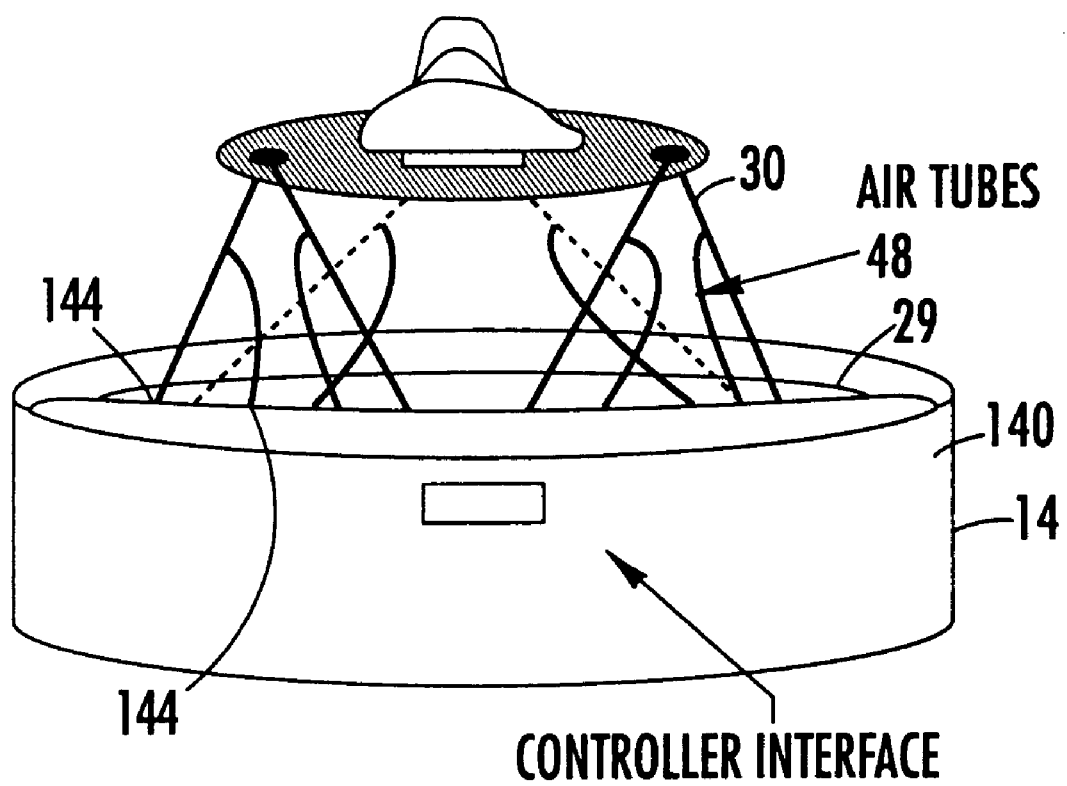
FIG. 11 is an alternative embodiment of rehabilitation device including an integral controller interface.

FIG. 11 illustrates an alternative embodiment of rehabilitation device 12 integral with controller interface 14. Controller interface 14 is housed in chassis 140. Chassis 140 is coupled to fixed platform 29. Alternatively, fixed platform 29 is integral with the upper surface of chassis 140. Air tubing 48 extends through apertures 144 in fixed platform 29. Air tubing 48 is coupled to linear actuator assemblies 30, as described above.

Figure 12:
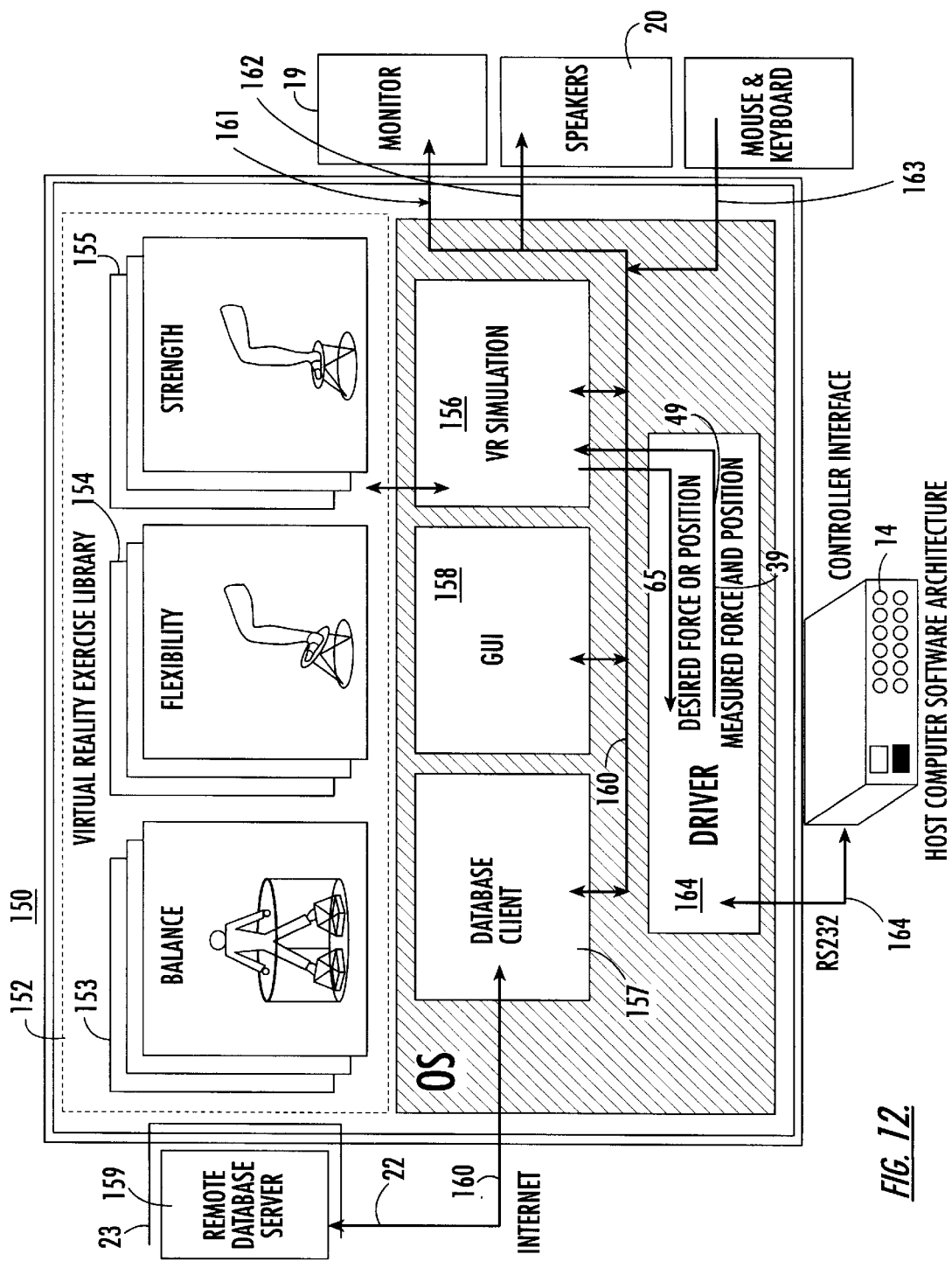
FIG. 12 is a schematic diagram of an architecture of the rehabilitation system.

FIG. 12 is a schematic diagram of an architecture of host computer 18 for providing a virtual reality interface to a user of rehabilitation device 12. For example, host computer 18 can be a Pentium personal computer. The virtual reality interface provides force feedback to a user of rehabilitation device 12 in response to a pseudo environment generated by host computer 18. Virtual reality exercise library 152 includes software modules to virtually represent exercises that can be performed by a user of rehabilitation device 12. For example, virtual reality exercise library 152 can include exercises for balance 153 including a virtual representation of a user balancing on one or two rehabilitation devices 12, exercises for flexibility 154 including a virtual representation of the user's ankle in a flexed position and exercises for strength 155 including a virtual representation of the application of pressure from the user to rehabilitation device 12.

As the user manipulates his related body parts to perform exercises in virtual reality library 152, mobile platform 25 of rehabilitation system 12 moves to a position simulated by virtual reality simulation 156 or applies appropriate force feedback to simulate forces applied in virtual reality simulation 156. For example, during exercises for balance 153 and exercises for flexibility 154, rehabilitation device 12 moves to a desired position. Alternatively, during exercises for strength 155, rehabilitation device 12 provides force feedback in six degrees of freedom for applying a desired resistive force to foot 11.

Exercises for flexibility 154 involve improving a user's range of motion by performing repetitive motions near the user's current limits of motion with little or no opposing forces. Preferably, during exercises for strength 155, force feedback is applied to rehabilitation device 12 up to a maximum value. A user applies force and torque to rehabilitation device 12 to try to overcome the applied force and torque feedback. Examples of simulations for improving both strength and flexibility include a racecar simulation in which rehabilitation device 12 acts as both an accelerator, break, and steering wheel. As the racecar moves down the track, pushing down against mobile platform 25 in the plantar flexion direction accelerates the car, pulling up in the dorsiflextion direction applies the breaks, and moving the foot from side-to-side steers the car around turns and obstacles. Other examples include a flying vehicle simulation in which rehabilitation device 12 controls the steering and acceleration of a hot air balloon, glider, or jet fighter. Moving mobile platform 25 guides the vehicle through a slalom course of floating hoops, runway landing, or air-to-air combat. An alternative example includes a simulation in which rehabilitation device 12 controls a first-person interactive shooting game in which patients must fight their way out of a dungeon guarded by monsters. Moving mobile platform 25 in certain directions fires a weapon, opens a door, or makes the simulated person character walk through the virtual world. Another example of an exercise is a simulation in which letter-shapes are traced using the virtual tip of foot 11 thereby moving mobile platform 25 accordingly.

Virtual reality simulation 156 of the exercises in virtual reality exercise library 152 is performed based on data related to the user 160 stored in client database 157 and parameters inputted from the user at graphical user interface (GUI) 158. For example, virtual reality simulation 156 can be developed with 3D World Simulation as provided in WorldToolKit manufactured by Engineering Animation, Inc. Simulation of conventional physic laws to determine actual movements of the related body parts can be used to develop virtual reality simulation 156. Data related to the user 160 can also be forwarded over network 22 from a remote database server 159 at remote computer 23. For example, data related to the user 160 can include a limit of the range of motion of foot 11 to limit the position of rehabilitation device 12, the amount of force feedback to be applied from rehabilitation device 12, the number of repetitions of exercises in virtual reality exercise library 152 to be performed by user 11. For example, remote database server 159 can provide similar data related to the user 160 that is stored in client database 157 or can provide diagnostic information such as an initial diagnosis. For example, the initial diagnosis can be a comparison of the user's information such as range of ankle motion with data for a human ankle without an injury. Parameters of the initial diagnosis are forwarded as data related to the user 160 to control virtual reality simulation 156. Virtual reality simulation 156 can be controlled to provide safeguards for preventing injury to user 160.

Virtual reality visual output 161 from virtual reality simulation 156 is displayed on display 19 and virtual reality audio output 162 from virtual reality simulation 156 is played on speakers 20. Mouse and keyboard interface 163 to virtual reality simulation 156 can be used in conjunction with graphical user interface 158 to allow the user to enter parameters, such as choosing, for example, which exercise from virtual reality exercise library 152 to perform and the number of repetitions or duration of the exercise.

Driver software 164 interfaces virtual reality simulation 156 and controller interface 14 for providing a level of abstraction for communication there between. Preferably, the inputs to driver 164 are desired force and positioning measurement data 65 from the virtual reality simulation 156, force measurement data 39 from controller interface 14, and position measurement data 49 from controller interface 14.

The outputs of driver 164 are desired force and position measurement data 65 transmitted to controller interface 14, measured force measurement data 39 forwarded to virtual reality simulation 156, and position measurement data 49 forwarded to virtual reality simulation 156.

Figure 13:
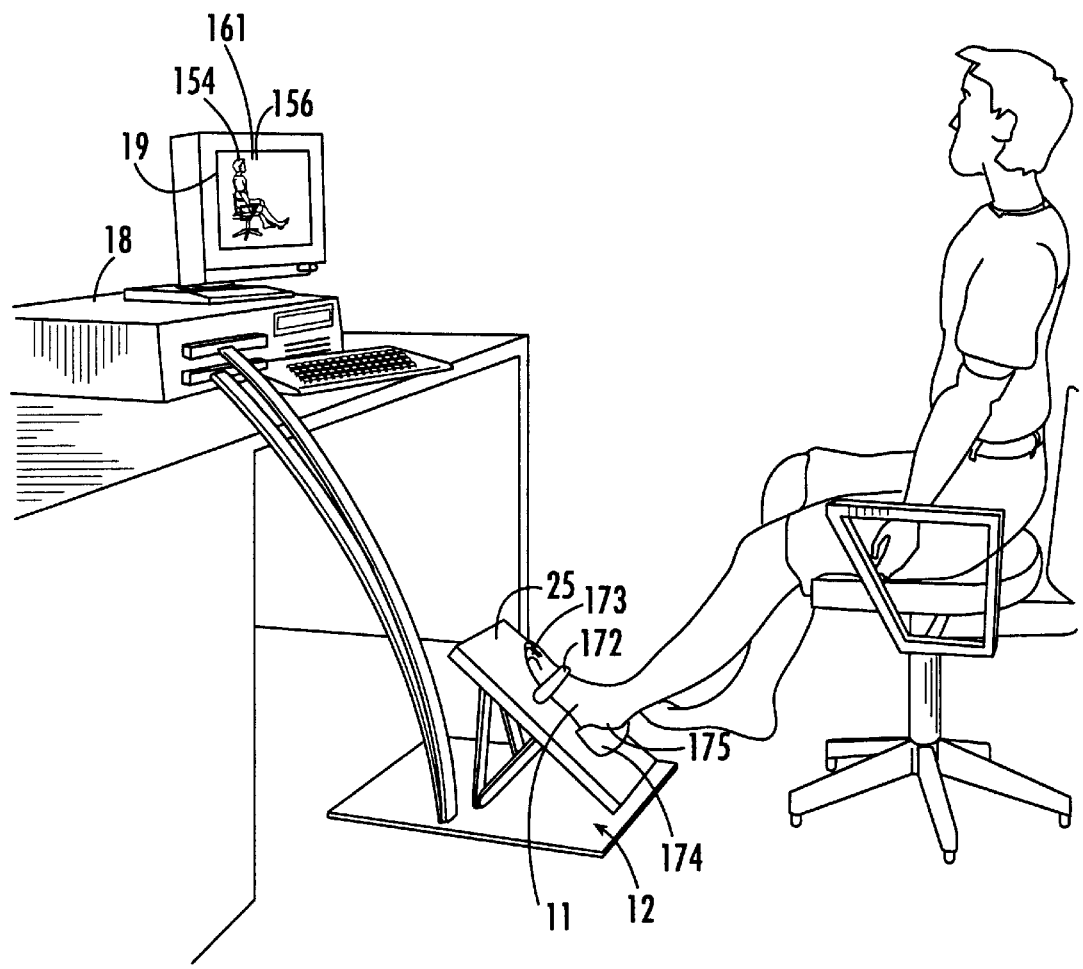
FIG. 13 is a perspective view of an interaction of a user with the rehabilitation device and a virtual reality simulation.

FIG. 13 is a perspective view of the interaction of a user with rehabilitation device 12 and virtual reality simulation 156. In this embodiment, foot attachment 24 can comprise u-shaped frame 172 attached to mobile platform 25 receiving toes 173 of foot 11 and u-shaped heel support 174 coupled to mobile platform 25 receiving heel 175 of foot 11.

A user has selected exercises for flexibility 154. Virtual reality simulation 156 provides virtual reality visual output 161 which is displayed on display 19 in which the user is virtually represented as sitting and interacting with rehabilitation device 12 for performing exercises for flexibility 154. Force feedback is applied to rehabilitation device 12 in six degrees of freedom to move rehabilitation device 12 to the desired position shown in virtual reality visual output 161 on display 19.

Figure 14A:
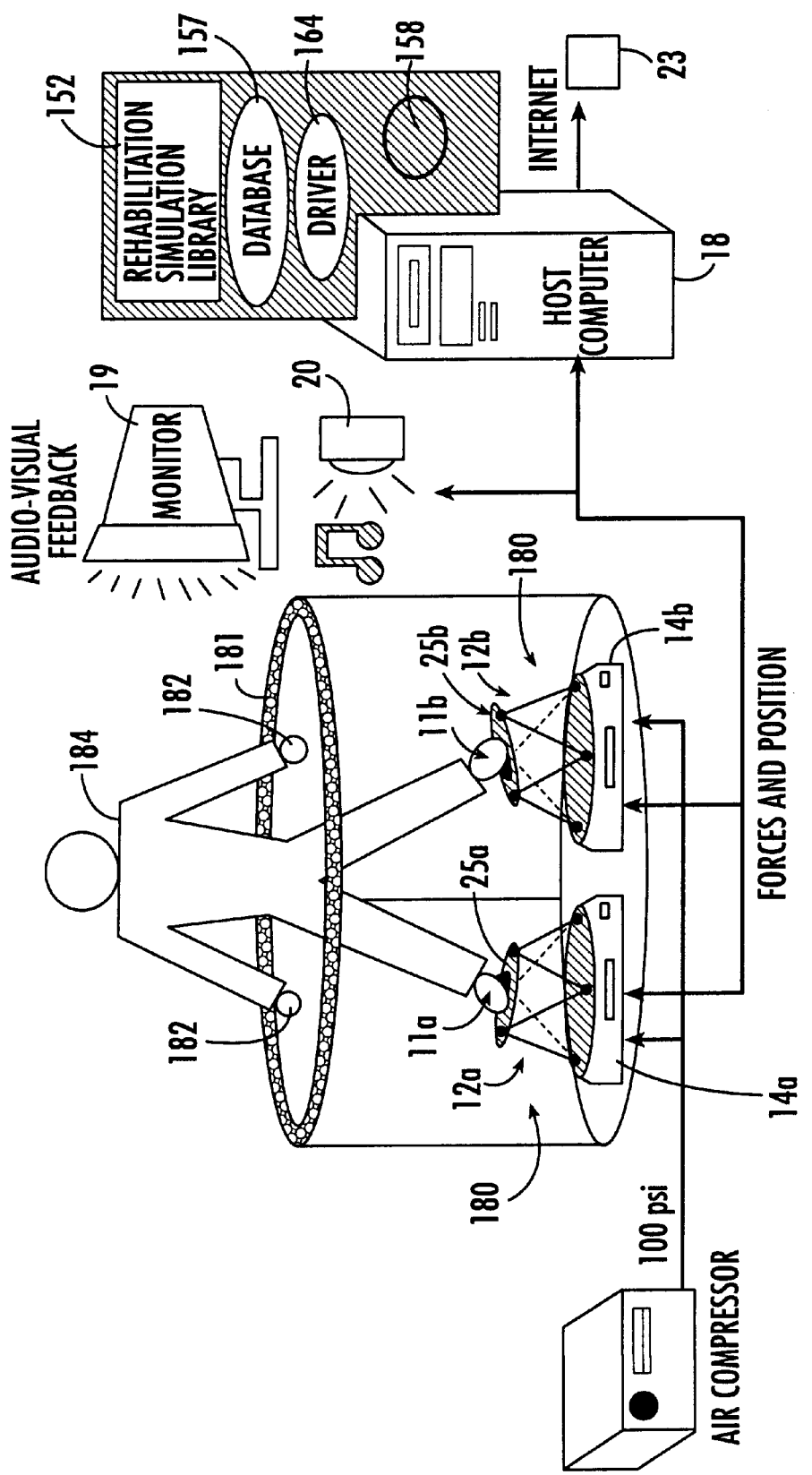
FIG. 14A is a perspective view of a system of simultaneous use of a pair of rehabilitation devices by a user.

FIGS. 14A and 14B illustrate an alternative embodiment of a system of simultaneous use of a pair of rehabilitation devices 180 with one rehabilitation device being used for each ankle 11a and 11b. Virtual reality simulation 156 provides simulations for performing exercises for balance 153 and simultaneously controlling rehabilitation devices 12a and 12b. Controller interface 14a interfaces rehabilitation device 12a and controller interface 14b interfaces rehabilitation device 12b. Measured positions and forces applied to foot 11a by rehabilitation device 12a and measured positions and forces applied to foot 11b by rehabilitation device 12b are received at respective controller interface 14a and controller interface 14b. Host computer 18 generates rehabilitation instructions to controller interface 14a and controller interface 14b. In certain embodiments, the desired position and forces of mobile platforms 25a and 25b are calculated together. For example, if a virtual simulation is to simulate a planar surface, each of mobile platforms 25a and 25b are planar. Virtual reality simulation 156 of platform objects can be performed by aggregating the platform object into a parent object whose position, orientation and forces are calculated. From the net values, each individual mobile platform 25a and 25b components can be calculated.

In this embodiment, rehabilitation devices 12a and 12b completely control the user's centers of gravity and the user's balance at all times. Low-level control software is implemented in controller interfaces 14a and 14b for defining and maintaining dynamic range of motion (ROM) constraints to prevent the user from falling off rehabilitation devices 12a and 12b. An adjustable, cushioned guard rail 181 can be positioned around rehabilitation devices 12a and 12b and held by hands 182 of user 184 to provide support to user 184 who loses their balance during coordination training. Rehabilitation devices 12a and 12b are also protected from overload based on bearing the weight of user 184. ROM constraints depend on both the desired difficulty of an exercise selected from virtual reality exercise library 152 and the weight of user 184. Difficulty parameters can be entered by user 184 through graphical user interface 158 or from remote computer 23 before exercises begin and forwarded to low-level control software of controller interfaces 14a and 14b. The weight of user 184 can either be measured by mobile platform 25 or entered by user 184 from graphical user interface 158. The low-level software of controller interface 14 continually maintains that rehabilitation devices 12a and 12b are within the defined ROM.

Examples of balance simulations include a surfing simulation in which patient's must maintain their balance on the pair of mobile platforms 25 as they ride the ocean's waves or ski down a ski slope.

Figures 15A, 15B:
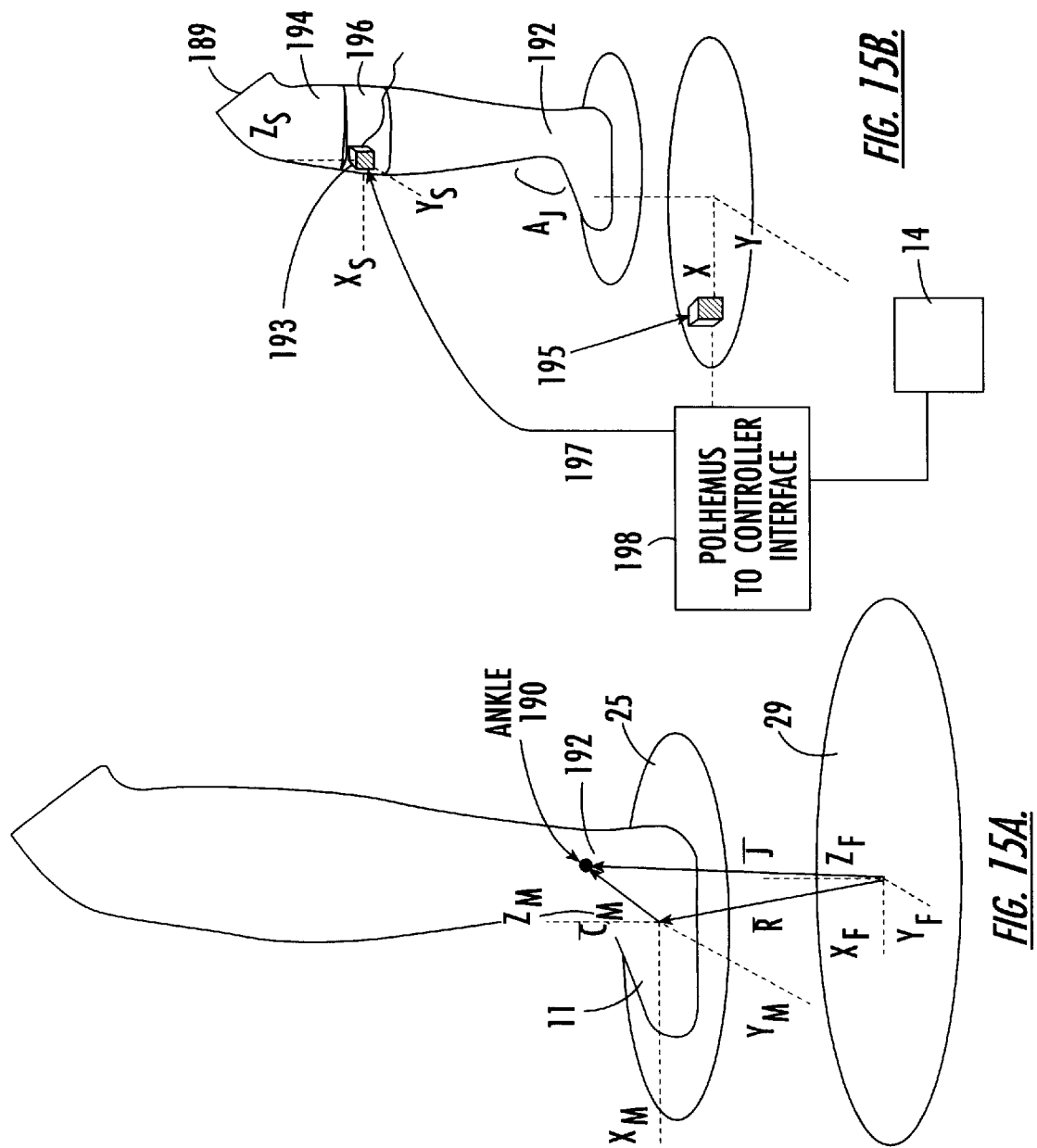
FIG. 15A is a schematic diagram of a mobile coordinate system and fixed coordinate system in relation to an ankle joint.
FIG. 15B is a schematic diagram of a system for calculating the angle of the ankle.

FIGS. 15A and 15B illustrate system for calculating the angle of the ankle 190 which can be used in combination with rehabilitation device 12. Fixed coordinate system of fixed platform 29 is represented by $x_F$, $y_F$ and $z_F$ at the center of fixed platform 29. Mobile coordinate system of mobile platform 25 is represented by $x_M$, $y_M$ and $z_M$ at the center of mobile platform 25. Position of ankle joint 192 is determined from the equation:

$$J = R + C_m$$

wherein J is a vector from the origin of the fixed coordinate system to the ankle joint, R is a vector from the origin of the fixed coordinate system to the origin of the mobile coordinate system and $C_m$ is a vector from the origin of the mobile coordinate system to the ankle joint. $C_m$ is dependent on dimensions of foot 11 and position of foot 11 relative to mobile platform 25. It will be appreciated that the dimensions of foot 11 can be calibrated for each user with conventional techniques.

Position sensor receiver 193 is coupled to leg 194 of user 184 with straps 196. Position sensor receiver 193 receives signals from position sensor transmitter 195. For example, position sensor receiver 193 and position sensor transmitter 195 can be a polhemus receiver and transmitter. Data 197 from position sensor receiver 193 is forwarded to sensor controller interface 198. Sensor controller interface 198 is coupled to controller interface 14. Controller interface 14 uses data 197 received from sensor controller interface 198 to calculate a measurement of angle $A_j$ between ankle joint 192 and mobile platform 25. Measurement of angle $A_j$ can be forwarded to host computer 18. Host computer 18 can apply input of a desired measurement of angle $A_j$ to controller interface 14. Controller interface 14 can apply force feed back using linear actuator assembly 30 to move mobile platform 25 to the desired measurement of angle $A_j$. Preferably, exercises for flexibility 154 can include the system for calculating the angle of the ankle 190 for accurate placement of foot 11 to achieve a desired position of ankle joint 192.

Figure 16:
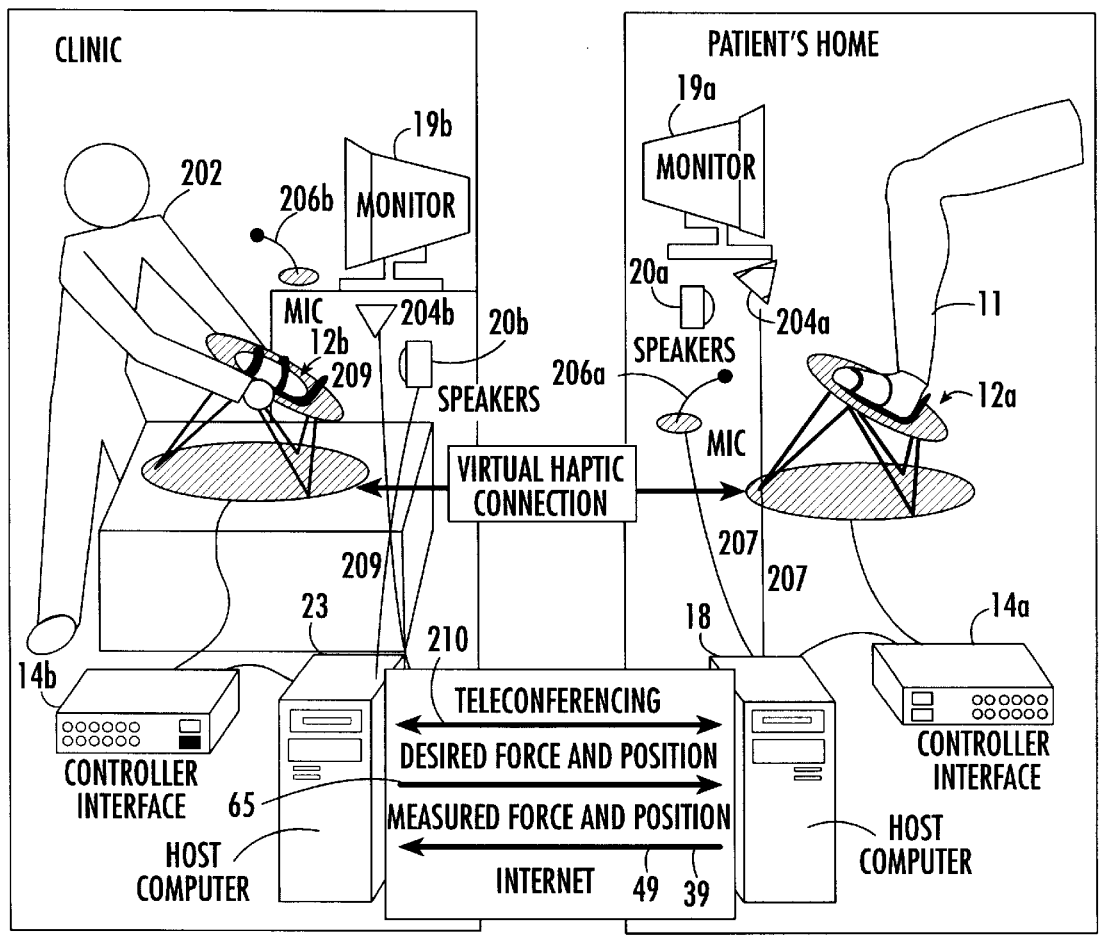
FIG. 16 is a schematic diagram of a system for interactive telerehabilitation.

FIG. 16 illustrates a system for interactive telerehabilitation 200. Controller interface 14a interfaces host computer 18 to rehabilitation device 12a. Position measurement data 49 and force measurement data 39 are sent over network 22 to remote computer 23. For example, network 22 can be the internet. Rehabilitation device 14b interfaces remote computer 23 to rehabilitation device 12b. User 202 manipulates rehabilitation device 12b to generate desired force and position measurement data 65. For example, user 202 can be a therapy specialist. Desired force and measurement data 65 is transferred to host computer 18 over network 22.

Video camera 204a and microphone 206a are positioned to record respective images and sounds at adjacent rehabilitation device 12a and provide signals 207 to host computer 18. Video camera 204b and microphone 206b are positioned to record respective images and sound at adjacent rehabilitation device 12b and provide signals 209 to host computer 23. Teleconferencing connection 210 connects host computer 18 and remote computer 23 for receiving and sending signals 207 and signals 209. Signals 207 transferred over teleconferencing connection 210 are displayed on monitor 19b and speakers 20b. Signals 209 transferred over teleconferencing connection 210 are displayed on monitor 19a and speakers 20a. System for interactive telerehabilitation 200 provides a virtual haptic connection between rehabilitation device 12a and remote rehabilitation device 12b.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

We claim:

1. An ankle rehabilitation system for rehabilitating an ankle of a user comprising:

a mobile platform adapted to be coupled to a foot of the user;

a fixed platform coupled to said mobile platform;

six linear actuator assemblies to determine a measured position of said mobile platform in relation to said fixed platform in six degrees of freedom each, of said linear actuator assemblies having an upper attachment end attached to said mobile platform and a lower attachment end attached to said fixed platform;

means for measuring force exerted by said foot against said mobile platform in six degrees of freedom; and means for controlling said mobile platform receiving said measured position of said mobile platform and said measured force exerted by said foot against said mobile platform and applying desired force feedback in six degrees of freedom to said mobile platform.

2. The ankle rehabilitation system of claim 1 wherein each of said linear actuator assemblies comprises:

a piston mounted in parallel with a position sensor, said position sensor measuring position of said piston.

3. The ankle rehabilitation system of claim 2 wherein said means for controlling said mobile platform comprises:

a controller interface coupled to said linear actuator assemblies and a computer system coupled to said controller interface wherein said controller interface receives said measured position and said measured force exerted by said foot against said mobile platform and forwards said measured position and said measured force exerted by said foot against said mobile platform to said computer system and said computer system generates said desired force feedback for moving said mobile platform to a desired position or for applying a desired force to said mobile platform.

4. The ankle rehabilitation system of claim 3 wherein said piston is an air piston, said piston is coupled with air tubing to said controller interface and wherein said controller interface is coupled to an air compressor and further comprises means for applying air pressure to said piston from said air compressor, thereby changing the length of said piston and the position of said mobile platform in relation to said fixed platform.

5. The ankle rehabilitation system of claim 4 wherein said piston is a dual acting piston having a pair of air compartments and said means for applying air pressure to said piston comprises an intake valve and an exhaust valve coupled to each of said air compartments.

6. The ankle rehabilitation system of claim 5 wherein said controller interface comprises:

a pressure sensor measuring the pressure in each of said air compartments, an analog to digital converter receiving the measured position of said piston and the measured pressure of said air compartments, a programmable computer system having a computer program for calculating large pressure changes and for calculating small pressure changes for increasing and decreasing pressure in said piston by opening or closing said intake valve and said exhaust valve based on the measured pressure of said air compartments and the measured position of said piston and the desired position of said piston or desired force of said piston to determine the relative position of mobile platform with respect to fixed platform or relative force to be applied to mobile platform.

7. The ankle rehabilitation system of claim 6 further comprising a computer program for force control to control said force feedback such that said force applied by said rehabilitation device on the foot is the same as the desired force.

8. The ankle rehabilitation system of claim 7 wherein each one of said linear actuator assemblies measures position of a respective shaft.

9. The ankle rehabilitation system of claim 8 wherein each pair of linear actuator assemblies are mounted in a V-shaped configuration between said mobile platform and said fixed platform.

10. The ankle rehabilitation system of claim 3 wherein said fixed platform is attached to a chassis housing said controller interface.

11. The ankle rehabilitation system of claim 1 wherein said means for measuring force exerted by said foot against said mobile platform comprises:

a force sensor coupled between said foot attachment and said mobile platform.

12. The ankle rehabilitation system of claim 1 further comprising:

tilt adjustment means for varying an angle $A_p$ between said fixed platform and a floor platform.

13. The ankle rehabilitation system of claim 1 wherein said means for controlling said mobile platform further comprises:

virtual reality simulation means for determining a virtual image of virtual objects moveable by said user to virtually simulate an exercise adapted to be performed by said user, wherein said desired force feedback is applied in six degrees of freedom to said mobile platform to move said mobile platform to a position represented by said virtual image or to apply a translation force or torque to said mobile platform represented by said virtual image.

14. The ankle rehabilitation system of claim 13 wherein said means for controlling said mobile platform further comprises:

a database for storing information of said user as user data and parameter input means for inputting parameters of said exercise, wherein said user data and said parameters are used in said virtual reality simulation means for determining said virtual image.

15. The ankle rehabilitation system of claim 14 wherein said user data is selected from the group consisting of a limit of a range of motion of said foot, an amount of said desired force feedback, and a number of repetitions of said exercises.

16. The ankle rehabilitation system of claim 15 further comprising means for controlling said virtual reality simulation to provide safeguards for preventing injury to the user.

17. The ankle rehabilitation system of claim 13 further comprising a remote database for storing information of said user remotely from said virtual reality simulation means as remote user data, said remote user data being applied over a network to said virtual reality simulation means and wherein said remote user information is used in said virtual reality simulation means for determining said virtual image.

18. The ankle rehabilitation system of claim 17 wherein said remote user data is selected from the group consisting of a limit of a range of motion of said foot, an amount of said desired force feedback, and a number of repetitions of said exercises and diagnostic information.

19. The ankle rehabilitation system of claim 13 wherein said exercise is a balancing exercise.

20. The ankle rehabilitation system of claim 13 wherein said exercise is a flexibility exercise.

21. The ankle rehabilitation system of claim 13 wherein said exercise is a strength exercise.

22. The ankle rehabilitation system of claim 1 further comprising:
- a second mobile platform adapted to be coupled to the other foot of the user;
- means for measuring a second measured position of said second mobile platform in relation to a second fixed platform in six degrees of freedom; and
- means for measuring a second force exerted by said other foot against said second mobile platform in six degrees of freedom, said means for controlling said mobile platform receiving said second measured position of said second mobile platform and said measured second force exerted by said other foot against said second mobile platform and applying second desired force feedback in six degrees of freedom to said second mobile platform.

23. The ankle rehabilitation system of claim 22 further comprising:
- virtual reality simulation means for determining a virtual image of virtual objects moveable by the user to virtually simulate an exercise adapted to be performed by a user of said system,
- wherein said desired force feedback and said second desired force feedback are applied to said mobile platform and said second mobile platform to move said mobile platform and said second mobile platform to a respective position represented by said virtual image and said exercise is a simulation of said user balancing on said mobile platform and said second mobile platform.

24. The system of claim 23 further comprising means for determining a dynamic range of motion constraint and said means for controlling said mobile platform receiving said dynamic range of motion constraint and applying desired force feedback within said dynamic range of motion constraint.

25. The system of claim 24 further comprising a guard rail positioned around said mobile platform and said second mobile platform.

26. The system of claim 1 further comprising means for calculating a position of an ankle joint of said user from the equation:

$$J=R+C_m$$

wherein J is a vector from an origin of a fixed coordinate system to an ankle joint, R is a vector from an origin of a fixed coordinate system to an origin of the mobile coordinate system and $C_m$ is a vector from the origin of the mobile coordinate system to the ankle joint.

27. The ankle rehabilitation system of claim 26 wherein said means for calculating position of an ankle joint comprises:
- a transmitter attached to said mobile platform transmitting a first signal;
- a receiver adapted to be attached to the leg of the user above said foot, said receiver receiving said first signal; and
- means for calculating the relative position according to said equation between said transmitter and receiver.

28. The ankle rehabilitation system of claim 1 further comprising:
- a second mobile platform adapted to be moved by a second user;
- means for measuring a second measured position of said second mobile platform in relation to a second fixed platform in six degrees of freedom and means for measuring a second measured force exerted by said second user; and
- means for forwarding said second measured position and second measured force exerted by said second user to said means for controlling said mobile platform, wherein said desired force feedback applied to said mobile platform is determined from said second measured position and said second measured force.

29. The ankle rehabilitation system of claim 28 further comprising:
- a first video camera and a first microphone for recording respective images and sound at said mobile platform to provide a first signal to a first computer system;
- a second video camera and a second microphone for recording respective images and sound at said second mobile platform to provide a second signal to a second computer system;
- a first output display means for displaying video and audio output at said mobile platform;
- a second output for display means displaying video and audio at said second mobile platform; and
- teleconferencing connection between said first computer system and said second computer system,
- wherein said first signal is transmitted to said second computer system for display on said second output display means and said second signal is transmitted to said first computer system for display on said first output display means.

30. A method for rehabilitating an ankle of a user comprising the steps of:
- coupling a mobile platform to a user's foot;
- measuring position of said mobile platform in relation to a fixed platform in six degrees of freedom,
- measuring force exerted by said foot against said mobile platform in six degrees of freedom; and
- controlling said mobile platform with said measured position of said mobile platform and said measured force exerted by said foot against said mobile platform by applying desired force feedback in six degrees of freedom to said mobile platform.

31. A method for telerehabilitating an ankle comprising the steps of:
- moving a first mobile platform at a remote therapist location;
- measuring position of said mobile platform in relation to a fixed platform in six degrees of freedom;
- measuring force exerted by said foot against said platform in six degrees of freedom,
- transmitting said measured position and measured force to a second mobile platform attached to a patient's foot; and
- moving said second mobile platform to said measured position and applying said measured force to said patient's foot.

* * * * *